(12) United States Patent
Schwarz et al.

(10) Patent No.: US 7,153,813 B2
(45) Date of Patent: Dec. 26, 2006

(54) SUBSTITUTED ARYL KETONES

(75) Inventors: Hans-Georg Schwarz, Langenfeld (DE); Mark Wilhelm Drewes, Langenfeld (DE); Peter Dahmen, Neuss (DE); Dieter Feucht, Eschborn (DE); Rolf Pontzen, Leichlingen (DE); Monika Schmitt, Frankfurt (DE)

(73) Assignee: Bayer Aktiengesellschaft, Monheim (DE)

( * ) Notice: Subject to any disclaimer, the term of this patent is extended or adjusted under 35 U.S.C. 154(b) by 0 days.

(21) Appl. No.: 10/504,743

(22) PCT Filed: Feb. 12, 2003

(86) PCT No.: PCT/EP03/01365

§ 371 (c)(1),
(2), (4) Date: Feb. 11, 2005

(87) PCT Pub. No.: WO03/070696

PCT Pub. Date: Aug. 28, 2003

(65) Prior Publication Data

US 2005/0119129 A1    Jun. 2, 2005

(30) Foreign Application Priority Data

Feb. 19, 2002 (DE) .................. 102 06 792

(51) Int. Cl.
*A01N 43/56* (2006.01)
*A01N 37/34* (2006.01)
*A01N 35/00* (2006.01)
*C07C 317/26* (2006.01)
*C07C 317/24* (2006.01)

(52) U.S. Cl. .......... 504/280; 504/310; 504/348; 548/369.4; 558/410; 568/42

(58) Field of Classification Search ........ 504/273, 504/280, 310, 348; 548/264.4, 369.4; 558/410; 568/42
See application file for complete search history.

(56) References Cited

U.S. PATENT DOCUMENTS

| | | | |
|---|---|---|---|
| 3,733,364 A | 5/1973 | Meschino et al. ...... 260/607 A |
| 4,780,127 A | 10/1988 | Michaely et al. ............ 71/103 |
| 4,806,146 A | 2/1989 | Carter .......................... 71/98 |
| 4,816,066 A | 3/1989 | Michaely et al. ............ 71/123 |
| 4,946,981 A | 8/1990 | Carter et al. ............... 558/415 |
| 4,986,845 A | 1/1991 | Oya et al. ..................... 71/92 |
| 5,006,158 A | 4/1991 | Carter et al. .................. 71/98 |
| 5,006,162 A | 4/1991 | Carter ........................ 71/123 |
| 5,085,688 A | 2/1992 | Michaely et al. ............ 71/103 |
| 5,110,343 A | 5/1992 | Ueda et al. ................... 71/88 |
| RE34,779 E | 11/1994 | Oya et al. ................... 504/282 |
| 5,371,063 A | 12/1994 | Cramp et al. ............... 504/270 |
| 5,374,606 A * | 12/1994 | Cramp et al. ............... 504/270 |
| 5,489,570 A | 2/1996 | Geach et al. ............... 504/261 |
| 5,650,533 A | 7/1997 | Roberts et al. ............... 560/17 |
| 5,656,573 A | 8/1997 | Roberts et al. ............. 504/271 |
| 5,747,424 A | 5/1998 | Roberts et al. ............. 504/271 |
| 5,804,532 A | 9/1998 | Cain et al. .................. 504/309 |
| 5,834,402 A | 11/1998 | Von Deyn et al. .......... 504/271 |
| 5,846,906 A | 12/1998 | von Deyn et al. .......... 504/221 |
| 5,846,907 A | 12/1998 | von Deyn et al. .......... 504/221 |
| 5,859,283 A | 1/1999 | Cramp ...................... 560/124 |
| 5,863,865 A | 1/1999 | Lee et al. ................... 504/271 |
| 5,948,917 A | 9/1999 | Adachi et al. .............. 548/247 |
| 5,998,334 A * | 12/1999 | Murai et al. ................ 504/282 |
| 6,004,903 A | 12/1999 | von Deyn et al. .......... 504/239 |
| 6,124,469 A | 9/2000 | Rheinheimer et al. ...... 548/240 |
| 6,153,759 A | 11/2000 | von Deyn et al. ......... 548/131 |
| 6,156,702 A | 12/2000 | Engel et al. ................ 504/282 |
| 6,156,944 A | 12/2000 | Pham et al. ................ 504/271 |
| 6,207,618 B1 | 3/2001 | Engel et al. ................ 504/282 |
| 6,297,198 B1 | 10/2001 | Lee ........................... 504/271 |
| 6,376,429 B1 | 4/2002 | Van Almsick et al. ...... 504/271 |
| 6,432,881 B1 | 8/2002 | Engel et al. ................ 504/280 |
| 6,559,100 B1 | 5/2003 | Engel et al. ................ 504/223 |
| 6,610,631 B1 * | 8/2003 | Muller et al. .............. 504/273 |

(Continued)

FOREIGN PATENT DOCUMENTS

CA          1314557          3/1993

(Continued)

OTHER PUBLICATIONS

Journal of Medicinal Chemistry, vol. 21, No. 6, (month unavailable) 1978, pp. 529-536, Arthur F. Klug et al, "Tricyclic Aryl-Substituted Anticoccidial Azauracils".

(Continued)

*Primary Examiner*—Thurman K. Page
*Assistant Examiner*—Chukwuma Nwaonicha
(74) *Attorney, Agent, or Firm*—Richard E. L. Henderson; Raymond J. Harmuth

(57) ABSTRACT

The invention relates to novel substituted aryl ketones of the formula (I)

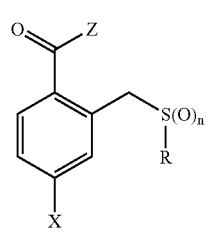

in which Z, X, R and n are as defined in the disclosure, to processes for their preparation and to their use as crop treatment agents, and to intermediates for preparing compounds of the formula (I).

7 Claims, No Drawings

U.S. PATENT DOCUMENTS

2002/0025910 A1    2/2002    Deyn et al.

FOREIGN PATENT DOCUMENTS

| CA | 2190001   | 11/1995 |
| CA | 2338304   | 2/2000  |
| CA | 2 252 543 | 1/2003  |
| EP | 0 609 798 | 8/1994  |
| WO | 97/27187  | 7/1997  |
| WO | 97/41106  | 11/1997 |
| WO | 97/46530  | 12/1997 |
| WO | 98/28981  | 7/1998  |
| WO | 99/03856  | 1/1999  |
| WO | 01/23367  | 4/2001  |

OTHER PUBLICATIONS

J. Org. Chem., vol. 36, No. 23, (month unavailable) 1971, pp. 3636-3638, Joseph A. Meschino et al, "The Reaction of p-Chlorobenzotrifluoride with Methylsulfinyl Carbanion".

* cited by examiner

SUBSTITUTED ARYL KETONES

The present patent application has been filed under 35 U.S.C. 371 as a national stage application of PCT/EP03/01365, filed Feb. 12, 2003, which was published in German as International Patent Publication WO 03/070696 on Aug. 28, 2003, and is entitled to the right of priority of German Patent Application 102 06 792.9, filed Feb. 19, 2002.

The invention relates to novel substituted aryl ketones, to processes for their preparation and to their use as crop treatment agents, in particular as herbicides.

It is already known that certain substituted aryl ketones have herbicidal properties (cf. EP-A-090 262, EP-A-135 191, EP-A-186 118, EP-A-186 119, EP-A-186 120, EP-A-319 075, EP-A-352 543, EP-A-418 175, EP-A-487 357, EP-A-527 036, EP-A-527 037, EP-A-560 483, EP-A-609 797, EP-A-609 798, EP-A-625 505, EP-A-625 508, EP-A-636 622, U.S. Pat. No. 5,804,532, U.S. Pat. No. 5,834,402, U.S. Pat. No. 5,846,906, U.S. Pat. No. 5,863,865, WO-A-95/31446, WO-A-96/26192, WO-A-96/26193, WO-A-96/26200, WO-A-96/26206, WO-A-97/27187, WO-A-97/35850, WO-A-97/41105, WO-A-97/41116, WO-A-97/41117, WO-A-97/41118, WO-A-97/43270, WO-A-97/46530, WO-A-98/28981, WO-A-98/31681, WO-A-98/31682, WO-A-99/03856, WO-A-99/07688, WO-A-99/07697, WO-A-99/10327, WO-A-99/10328, WO-A-00/05221, WO-A-00/21924). However, the activity of these compounds is not entirely satisfactory.

This invention now provides the novel substituted aryl ketones of the formula (I)

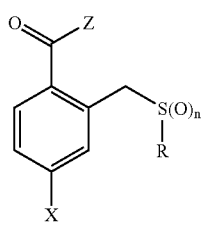

in which n represents the number 0, 1 or 2,

R represents in each case optionally substituted alkyl, alkenyl, alkynyl, cycloalkyl, cycloalkylalkyl, aryl or arylalkyl, X represent hydrogen, nitro, cyano, carboxy, carbamoyl, thiocarbamoyl, halo, or represents in each case optionally substituted alkyl, alkoxy, alkylthio, alkylsulphinyl, alkylsulphonyl, alkylamino, dialkylamino or dialkylaminosulphonyl, and Z represents one of the groupings below

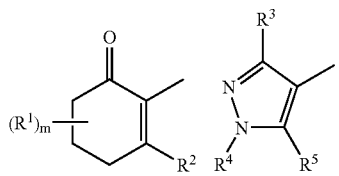

where m represents the number 0 to 6, $R^1$ represents hydrogen, halogen or represents in each case optionally substituted alkyl, alkylthio or aryl, or—if m represents the numbers 2 to 6—optionally also together with a second radical $R^1$ represents oxygen or alkanediyl (alkylene), $R^2$ represents hydroxyl, formyloxy, halogen, or represents in each case optionally substituted alkoxy, alkylthio, alkylsulphinyl, alkylsulphonyl, alkylcarbonyloxy, alkoxycarbonyloxy, alkylaminocarbonyloxy, alkylsulphonyloxy, alkenyloxy, alkynyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl, arylalkylsulphonyl or represents heterocyclyl which is attached via nitrogen, $R^3$ represents hydrogen, cyano, carbamoyl, thiocarbamoyl, halogen, or represents in each case optionally substituted alkyl, alkoxy, alkylthio, alkylsulphinyl, alkylsulphonyl, alkoxycarbonyl or cycloalkyl, $R^4$ represents hydrogen or represents in each case optionally substituted alkyl, alkenyl, alkynyl, cycloalkyl, cycloalkylalkyl, aryl or arylalkyl, and $R^5$ represents hydroxyl, formyloxy, or represents in each case optionally substituted alkoxy, alkylcarbonyloxy, alkoxycarbonyloxy, alkylaminocarbonyloxy, alkylsulphonyloxy, alkenyloxy, alkynyloxy, arylalkoxy, arylcarbonyloxy, arylcarbonylalkoxy or arylsulphonyloxy.

In the definitions, the hydrocarbon chains, such as alkyl or alkanediyl, are in each case straight-chain or branched—including in combination with hetero atoms, such as in alkoxy.

If the compounds of the general formula (I) can exist in different tautomeric or stereoisomeric forms, the invention includes the tautomeric or stereoisomeric forms possible in each case.

Preferred substituents or preferred ranges of the radicals present in the formulae given above and below are defined below.

n preferably represents the number 0 or 2.

R preferably represents optionally cyano-, halogen-, $C_1$–$C_4$-alkoxy-, $C_1$–$C_4$-alkylthio-, $C_1$–$C_4$-alkylsulphinyl or $C_1$–$C_4$-alkylsulphonyl-substituted alkyl having 1 to 6 carbon atoms, or represents in each case optionally cyano- or halogen-substituted alkenyl or alkynyl having in each case 2 to 6 carbon atoms, or represents in each case optionally cyano-, halogen- or $C_1$–$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, or represents in each case optionally nitro-, cyano-, halogen-, $C_1$–$C_4$-alkyl-, $C_1$–$C_4$-haloalkyl-, $C_1$–$C_4$-alkoxy- or $C_1$–$C_4$-haloalkoxy-substituted aryl or arylalkyl having in each case 6 or 10 carbon atoms in the aryl group and, if appropriate, 1 to 4 carbon atoms in the alkyl moiety.

X preferably represents hydrogen, nitro, cyano, carboxyl, carbamoyl, thiocarbamoyl, halogen, or represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl, alkylsulphonyl, alkylamino, dialkylamino or dialkylaminosulphonyl having in each case 1 to 6 carbon atoms in the alkyl groups.

m preferably represents the number 0, 1, 2 or 3.

$R^1$ preferably represents hydrogen, halogen, preferably represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl or alkylthio having in each case 1 to 6 carbon atoms, or represents phenyl, or—if m represents 2 or 3—optionally also together with a second radical R represents oxygen or alkanediyl (alkylene) having 3 to 5 carbon atoms.

$R^2$ preferably represents hydroxyl, formyloxy, halogen, preferably represents in each case optionally cyano-, halogen-, $C_1$–$C_4$-alkoxy-, $C_1$–$C_4$-alkoxy-carbonyl-, $C_1$–$C_4$-alkylthio-, $C_1$–$C_4$-alkylsulphinyl- or $C_1$–$C_4$-alkylsulphonyl-substituted alkoxy, alkylthio, alkylsulphinyl, alkylsulphonyl, alkylcarbonyloxy, alkoxycarbonyloxy, alkylaminocarbonyloxy or alkylsulphonyloxy having in each case 1 to 6 carbon atoms, preferably represents in each case optionally halogen-substituted alkenyloxy or alkynyloxy having in each case 3 to 6 carbon atoms.

preferably represents in each case optionally nitro-, cyano-, halogen-, $C_1$–$C_4$-alkyl-, $C_1$–$C_4$-haloalkyl-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkylsulphinyl-, $C_1$–$C_4$-haloalkylsulphinyl-, $C_1$–$C_4$-alkylsulphonyl- or $C_1$–$C_4$-haloalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl or arylalkylsulphonyl having in each case 6 or 10 carbon atoms in the aryl group and, if appropriate, 1 to 4 carbon atoms in the alkyl moiety, or preferably represents pyrrolyl, pyrazolyl, imidazolyl, triazolyl, tetrazolyl, each of which is attached via nitrogen.

$R^3$ preferably represents hydrogen, cyano, carbamoyl, thiocarbamoyl, halogen, preferably represents in each case optionally cyano-, halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl, alkoxy, alkylthio, alkylsulphinyl, alkylsulphonyl or alkoxycarbonyl having in each case 1 to 6 carbon atoms in the alkyl groups, or preferably represents optionally cyano-, halogen- or $C_1$–$C_4$-alkyl-substituted cycloalkyl having 3 to 6 carbon atoms $R^4$ preferably represents hydrogen, preferably represents optionally cyano-halogen-, $C_1$–$C_4$-alkoxy-, $C_1$–$C_4$-alkylthio-, $C_1$–$C_4$-alkylsulphinyl- or $C_1$–$C_4$-alkylsulphonyl-substituted alkyl having 1 to 6 carbon atoms, preferably represents in each case optionally cyano- or halogen-substituted alkenyl or alkynyl having in each case 3 to 6 carbon atoms, preferably represents in each case optionally cyano-, halogen- or $C_1$–$C_4$-alkyl-substituted cycloalkyl or cycloalkylalkyl having in each case 3 to 6 carbon atoms in the cycloalkyl group and, if appropriate, 1 to 4 carbon atoms in the alkyl moiety, or preferably represents in each case optionally nitro-, cyano-, halogen-, $C_1$–$C_4$-alkyl-, $C_1$–$C_4$-haloalkyl-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkylsulphinyl-, $C_1$–$C_4$-haloalkylsulphinyl-, $C_1$–$C_4$-alkylsulphonyl- or $C_1$–$C_4$-haloalkylsulphonyl-substituted aryl or arylalkyl having in each case 6 or 10 carbon atoms in the aryl group and, if appropriate, 1 to 4 carbon atoms in the alkyl moiety.

$R^5$ preferably represents hydroxyl, formyloxy, preferably represents in each case optionally cyano-, halogen- or $C_1$–$C_4$-alkoxy-substitued alkoxy, alkylcarbonyloxy, alkoxycarbonyloxy, alkylaminocarbonyloxy or alkylsulphonyloxy having in each case 1 to 6 carbon atoms in the alkyl groups, preferably represents in each case optionally cyano- or halogen-substituted alkenyloxy or alkynyloxy having in each case 3 to 6 carbon atoms or, preferably represents in each case optionally nitro-, cyano-, halogen-, $C_1$–$C_4$-alkyl-, $C_1$–$C_4$-haloalkyl-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkylsulphinyl-, $C_1$–$C_4$-haloalkylsulphinyl-, $C_1$–$C_4$-alkylsulphonyl- or $C_1$–$C_4$-haloalkylsulphonyl-substituted arylalkoxy, arylcarbonyloxy, arylcarbonylalkoxy or arylsulphonyloxy having in each case 6 or 10 carbon atoms in the aryl group and, if appropriate, 1 to 4 carbon atoms in the alkyl moiety.

n particularly preferably represents the number 2.

R particularly preferably represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl- and/or n- or i-propylsulphonyl-substituted methyl, ethyl, n- or i-propyl, n-, i-, s- or t-butyl, n-, i-, s- or t-pentyl, particularly preferably represents in each case optionally cyano-, fluorine-, chlorine- and/or bromine-substituted ethenyl, propenyl, butenyl, pentenyl, ethynyl, propynyl, butynyl or pentynyl, particularly preferably represents in each case optionally cyano-, fluorine-, chlorine-, bromine-, methyl-, ethyl- and/or n- or i-propyl-substituted cyclopropyl, cyclobutyl, cyclopentyl, cyclohexyl, cyclopropylmethyl, cyclobutylmethyl, cyclopentylmethyl or cyclohexylmethyl, or particularly preferably represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy- and/or trifluoromethoxy-substituted phenyl, naphthyl, phenylmethyl, phenylethyl or phenylpropyl.

X particularly preferably represents hydrogen, nitro, cyano, carboxyl, carbamoyl, thiocarbamoyl, fluorine, chlorine, bromine, iodine, or particularly preferably represents in each case optionally cyano-, fluorine-, chlorine-, methoxy-, ethoxy-, methylthio-, ethylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

m particularly preferably represents the number 0, 1 or 2.

$R^1$ particularly preferably represents hydrogen, fluorine, chlorine or bromine, represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methylthio, ethylthio, n- or i-propylthio, n-, i-, s- or t-butylthio, or represents phenyl, or—if m represents 2—optionally also together with a second radical $R^1$ represents oxygen, propane-1,3-diyl or butane-1,4-diyl.

$R^2$ particularly preferably represents hydroxyl, formyloxy, fluorine or chlorine, particularly preferably represents in each case optionally cyano-, fluorine-, chlorine-, methoxy-, ethoxy-, n- or i-propoxy-, methoxycarbonyl-, ethoxycarbonyl-, n- or i-propoxycarbonyl-, methylthio-, ethylthio-, n- or i-propylthio-, methylsulphinyl-, ethylsulphinyl-, methylsulphonyl- or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, particularly preferably represents in each case optionally fluorine-, chlorine- and/or bromine-substituted propenyloxy, butenyloxy, propynyloxy or butynyloxy, particularly preferably represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl or phenylmethylsulphonyl or particularly preferably represents pyrazolyl, imidazolyl, triazolyl, each of which is attached via nitrogen.

$R^3$ particularly preferably represents hydrogen, cyano, carbamoyl, thiocarbamoyl, fluorine, chlorine, bromine, particularly preferably represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or particularly preferably represents in each case optionally cyano-, fluorine-, chlorine-, methyl- or ethyl-substituted cyclopropyl, cyclobutyl, cyclopentyl or cyclohexyl.

$R^4$ particularly preferably represents hydrogen, particularly preferably represents in each case optionally cyano-, fluorine-, chlorine-, methoxy-, ethoxy-, n- or i-propoxy-, methylthio-, ethylthio-, n-or i-propylthio-, methylsulphinyl-, ethylsulphinyl-, methylsulphonyl- or ethylsulphonyl-substituted methyl, ethyl, n- or i-propyl, n-, i-, s- or t-butyl, particularly preferably represents in each case optionally cyano-, fluorine-, chlorine- and/or bromine-substituted propenyl, butenyl, propynyl or butynyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or particularly preferably represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyl or phenylmethyl.

$R^1$ particularly preferably represents hydroxyl, formyloxy, particularly preferably represents in each case optionally cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, particularly preferably represents in each case optionally cyano-, fluorine-, chlorine- and/or bromine-substituted propenyloxy, butenyloxy, propinyloxy or butinyloxy, or particularly preferably represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy.

R very particularly preferably represents in each case optionally fluorine- and/or chlorine-substituted methyl, ethyl, n- or i-propyl, n-, i- or s-butyl, very particularly preferably represents in each case optionally fluorine-, chlorine- or methyl-substituted cyclopropyl, cyclopentyl or cyclohexyl, or very particularly preferably represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy- or trifluoromethoxy-substituted phenyl or phenylmethyl.

X very particularly preferably represents nitro, cyano, carbamoyl, thiocarbamoyl, fluorine, chlorine, bromine, iodine, or very particularly preferably represents in each case optionally fluorine-, chlorine-, methoxy-, ethoxy-, methylthio-, ethylthio-, methylsulphinyl-, ethylsulphinyl-, methylsulphonyl- and/or ethylsulphonyl-substituted methyl, ethyl, methoxy, ethoxy, methylthio, ethylthio, methylsulphinyl, ethylsulphinyl, methylsulphonyl, ethylsulphonyl, dimethylamino or dimethylaminosulphonyl.

m very particularly preferably represents the number 0, $R^1$ very particularly preferably represents hydrogen, very particularly preferably represents in each case optionally fluorine- or chlorine-substituted methyl, ethyl, n- or i-propyl, methylthio, ethylthio, n- or i-propylthio, or represents phenyl, or—if m represents 2—optionally also together with a second radical $R^1$ represents oxygen, propane-1,3-diyl or butane-1,4-diyl.

$R^2$ very particularly preferably represents hydroxyl, very particularly preferably represents in each case optionally fluorine- or chlorine-substituted methoxy, ethoxy, n- or i-propoxy, methoxycarbonyl, ethoxycarbonyl, n- or i-propoxycarbonyl, methylthio, ethylthio, n- or i-propylthio, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, very particularly preferably represents in each case optionally fluorine-, chlorine- and/or bromine-substituted propenyloxy, butenyloxy, propynyloxy or butynyloxy, very particularly preferably represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyloxy, phenylthio, phenylcarbonyloxy, phenylcarbonylmethoxy, phenylsulphonyloxy, phenylmethoxy or phenylmethylthio or very particularly preferably represents pyrazolyl or imidazolyl, each of which is attached via nitrogen.

$R^3$ very particularly preferably represents hydrogen, fluorine, chlorine, bromine, very particularly preferably represents in each case optionally fluorine- or chlorine-substituted methyl, ethyl, n- or i-propyl, methoxy, ethoxy, n- or i-propoxy, methylthio, ethylthio, n- or i-propylthio, methylsulphinyl, ethylsulphinyl, methylsulphonyl, ethylsulphonyl, methoxycarbonyl, ethoxycarbonyl, n- or i-propoxycarbonyl, or very particularly preferably represents in each case optionally fluorine-, chlorine- or methyl-substituted cyclopropyl.

$R^4$ very particularly preferably represents hydrogen, very particularly preferably represents in each case optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl- or ethylsulphonyl-substituted methyl, ethyl, n- or i-propyl, n-, i-, s- or t-butyl, very particularly preferably represents in each case optionally fluorine-, chlorine- and/or bromine-substituted propenyl, butenyl, propynyl or butynyl, represents in each case optionally fluorine-, chlorine- or methyl-substituted cyclopropyl, cyclobutyl, cyclopentyl, cyclohexyl, cyclopropylmethyl, cyclobutylmethyl, cyclopentylmethyl or cyclohexylmethyl, or very particularly preferably represents in each case optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenyl or phenylmethyl.

$R^5$ very particularly preferably represents hydroxyl, very particularly preferably represents in each case optionally fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, very particularly preferably represents in each case optionally fluorine-, chlorine- and/or bromine-substituted propenyloxy, butenyloxy, propynyloxy or butynyloxy, or very particularly preferably represents in each case optionally nitro-, cyano-, fluorine-, chlorine-, bromine-, methyl-, ethyl-, n- or i-propyl-, trifluoromethyl-, methoxy-, ethoxy-, n- or i-propoxy, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl- or trifluoromethylsulphonyl-substituted phenylmethoxy, phenylcarbonyloxy, phenylcarbonylmethoxy or phenylsulphonyloxy.

X most preferably represents fluorine, chlorine, bromine, iodine, methoxy, methylthio, methylsulphonyl or trifluoromethyl.

R most preferably represents methyl, ethyl, n-propyl, i-propyl, n-butyl, i-butyl, t-butyl, 1,1,1-trifluoroethyl or phenyl.

$R^1$ most preferably represents hydrogen or methyl.

$R^2$ most preferably represents hydroxyl, chlorine or n-pyrazolyl.

$R^3$ most preferably represents hydrogen or methyl.

$R^4$ most preferably represents methyl or ethyl.

$R^5$ most preferably represents hydroxyl, propargyloxy, n-propylsulphonyloxy, tosyloxy, (benzoyl)methoxy, (ethoxycarbonyl)methoxy, or represents optionally fluorine-, chlorine-, bromine-, methyl- or trifluoromethyl-substituted benzyloxy.

Particular emphasis is given to compounds of the formula (I) in which

R represents optionally fluorine-, chlorine-, nitro-, or cyano-substituted methyl, ethyl, n-, i-propyl, n-, i-, s-, t-butyl, cyclopropyl, cyclopentyl, cyclohexyl, allyl, propargyl, benzyl or phenyl, X represents fluorine, chlorine, bromine, fluoromethyl, difluoromethyl, trifluoromethyl or nitro, n represents 0 or 2 and Z is as defined above.

Particular emphasis is also given to compounds of the formula (I) in which

R represents methyl, x represents trifluoromethyl, n represents 2 and

Z is as defined above.

Particular emphasis is also given to compounds of the formula (I) in which

R represents methyl,

X represents bromine, n represents 2 and

Z is as defined above.

Particular mention may be made of compounds of the formula (Ia)

(Ia)

in which n, X, R, $R^3$ and $R^4$ are as defined above.

Particular mention may furthermore be made of compounds of the formula (Ib)

(Ib)

in which n, X, R, $R^3$ and $R^4$ are as defined above and $R^{5'}$ has the meanings mentioned above for $R^5$, except for hydroxyl.

Particular mention may furthermore be made of compounds of the formula (Ic),

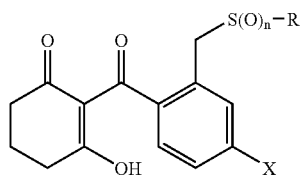

in which
n, X and R are as defined above.

Particular mention may further be made of compounds of the formula (Id).

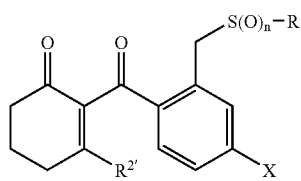

in which
n, X and R are as defined above, and
R² has the meanings mentioned above for R², except for hydroxyl.

The abovementioned definitions of the substituents can be combined with one another as desired. Moreover, individual definitions may not apply.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

The abovementioned general or preferred radical definitions apply both to the end products of the formula (I) and, correspondingly, to the starting materials or intermediates required in each case for the preparation.

These radical definitions can be combined with one another as desired, i.e. including combinations between the given preferred ranges.

The novel substituted aryl ketones of the formula (I) have strong and selective herbicidal activity.

The novel substituted aryl ketones of the formula (I) are obtained when carboxylic acids of the general formula (II)

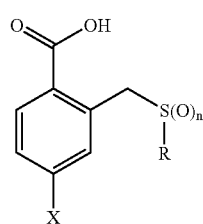

in which
n, R and X are as defined above
or reactive derivatives thereof, such as, for example, the corresponding acid halides, acid cyanides or esters
are reacted with compounds of the general formula (III)

H-Z   (III)

in which
Z is as defined above, if appropriate in the presence of a dehydrating agent and if appropriate in the presence of one or more reaction auxiliaries and if appropriate in the presence of one or more diluents, and, if appropriate, the compounds of the general formula (I) obtained after the process according to the invention has been carried out are subjected to subsequent reactions (for example substitution, oxidation or reduction reactions) in the context of substituent definition for conversion into other compounds of the general formula (I) according to customary methods.

Using, for example, 4-chloro-2-(ethylsulphinylmethyl) benzoic acid and cyclohexan-1,3-dione as starting materials, the course of the reaction in the process according to the invention can be illustrated by the formula scheme below:

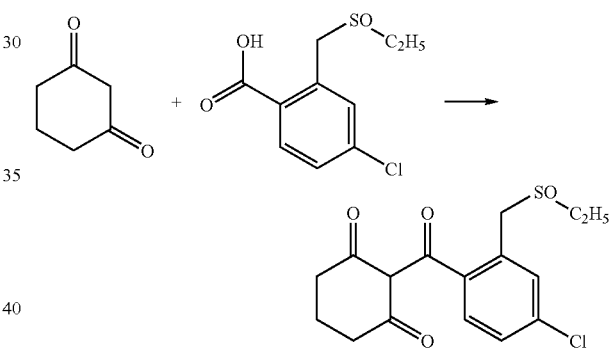

The formula (II) provides a general definition of the carboxylic acids to be used as starting materials in the process according to the invention for preparing compounds of the general formula (I). In the general formula (II), n, R, and X preferably have those meanings which have already been mentioned above, in connection with the description of the compounds of the general formula (I) according to the invention, as being preferred, particularly preferred, very particularly preferred or most preferred for n, R and X.

Some of the starting materials of the general formula (II) are known and/or can be prepared by processes known per se (cf. J. Med. Chem. 21 (1978), 529–536; J. Org. Chem. 36 (1971), 3636–3638; DE-A-20 65 636; U.S. Pat. No. 3,733,364; Preparation Examples). Individual compounds of the formula (U) are novel and form part of the subject-matter of the present application.

The formula (III) provides a general definition of the compounds further to be used as starting materials in the process according to the invention for preparing compounds of the general formula (I). In the general formula (III), Z preferably has those meanings which have already been mentioned above, in connection with the description of the compounds of the general formula (I) according to the invention, ash being preferred, particularly preferred, very particularly preferred or most preferred for Z. The starting materials of the general formula (III) are known organic chemicals for synthesis.

The process according to the invention for preparing the compounds of the formula (I) is preferably carried out using one or more reaction auxiliaries. Suitable reaction auxiliaries are, in general, the customary inorganic or organic bases or acid acceptors. These preferably include alkali metal or alkaline earth metal acetates, amides, carbonates bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate, or calcium carbonate, sodium bicarbonate, potassium bicarbonate or calcium bicarbonate, lithium hydride, sodium hydride potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiusopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, N-ethylpiperidine, N-methylmorpholine, N-ethylmorpholine, 1,4-diazabicyclo[2.2.2]octane (DABCO), 1,5-diazabicyclo[4.3.0]non-5-ene (DBN), or 1,8-diazabicyclo[5.4.0]undec-7-ene (DBU).

The process according to the invention is, if appropriate, carried out using a dehydrating agent. Suitable dehydrating agents are the chemicals customarily used for binding water.

Examples which may be mentioned are dicyclohexylcarbodiimide, carbonylbisimidazole and propanephosphonic anhydride.

Dehydrating agents which may be mentioned as being particularly suitable are dicyclohexylcarbodiimide and propanephosphonic anhydride.

The process according to the invention for preparing the compounds of the general formula (I) is preferably carried out using one or more diluents. Suitable diluents are especially inert organic solvents. These include, in particular, aliphatic, alicyclic or aromatic, optionally halogenated hydrocarbons, such as, for example, benzene, benzine, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide.

When carrying out the process according to the invention, the reaction temperatures can be varied within a relatively wide range. In general, the process is carried out at temperatures between 0° C. and 150° C., preferably between 10° C. and 120° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of a reaction auxiliary, and the reaction mixture is generally stirred at the required temperature for a number of hours. Work-up is carried out using customary methods (cf. the Preparation Examples).

The compounds of the formula (II)

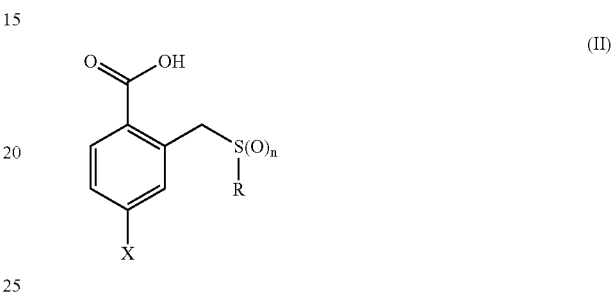

in which
X represents $CF_3$,
n and R are as defined above, are novel and also form part of the subject-matter of the present application.

Particular preference is given to compounds of the formula (II) in which
X represents $CF_3$,
n represents 0, 1 or 2 and
R represents methyl.

Particular preference is also given to compounds of the formula (II) in which
X represents bromine,
n represents, 0, 1 or 2 and
R represents methyl.

The compounds of the formula (VI)

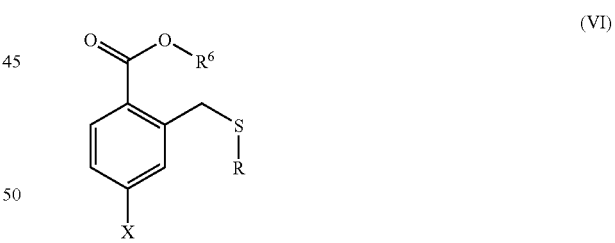

in which
X represents $CF_3$,
$R^6$ represents alkyl, benzyl or allyl, and
R is as defined above, are novel and also form part of the subject-matter of the present application.

Particular preference is given to compounds of the formula (VI) in which
X represents $CF_3$,
$R^6$ represents methyl, ethyl, allyl or benzyl and
R represents methyl, ethyl, allyl or benzyl.

The novel compounds of the formula (II) and (VI) are suitable for preparing active compounds for pharmaceutical, biological and agricultural purposes. They are particularly suitable for preparing compounds of the formula (I).

The novel carboxylic acids of the general formula (II) are obtained when halomethylbenzoic esters of the general formula (IV)

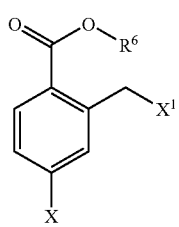
(IV)

in which
X is as defined above,
R⁶ represents alkyl (in particular methyl or ethyl), benzyl or allyl, and
X¹ represents halogen (in particular chlorine or bromine), are reacted with mercapto compounds of the general formula (V),

HS—R    (V)

in which
R is as defined above
or with alkali metal salts, such as sodium salts or potassium salts, of compounds of the formula (V)-, if appropriate in the presence of one or more reaction auxiliaries, such as, for example, potassium carbonate, triethylamine or sodium hydride, and if appropriate in the presence of one or more diluents, such as, for example, tetrahydrofuran, aceto-nitrile or N,N-dimethylformamide, at temperatures between 0° C. and 150° C., and the resulting carboxylic esters of the general formula (VI)

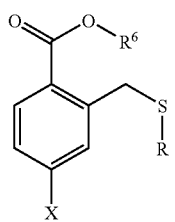
(VI)

in which
R, R⁶ and X are as defined above are, if appropriate, reacted with oxygenating agents, such as, for example, hydrogen peroxide, if appropriate in the presence of one or more diluents, such as, for example, acetic acid and/or water, at temperatures between 0° C. and 120° C., and the resulting esters are converted by customary methods, for example by reaction with aqueous sodium hydroxide and subsequently with hydrochloride acid, into the carboxylic acids of the formula (II) (cf. the Preparation Examples).

Some of the compounds of the formula (VI) are known, and/or they can be prepared by known processes. Individual compounds of the formula (VI) are novel and also form part of the subject-matter of the present application.

The active compounds according to the invention can be used as defoliants, desiccants, haulm killers and, in particular, as weed killers. Weeds in the broadest sense are to be understood as meaning all plants which grow in locations where they are undesired. Whether the substances according to the invention act as nonselective or as selective herbicides depends essentially on the amount used.

For example, the active compounds according to the invention can be used in the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desrodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thiaspi, Trifolium, Urtica, Veronica, Viola, Xanthium.*

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.*

Monocotyledenous weeds of the genera: *Aegilops, Agropyron, Agrostis, Alopecurus, Apera, Avena, Brachlaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Monocotyledenous crops of the genera: *Allium, Ananas, Asparagus, Avena, Hordeum, Oryza, Panicum, Saccharum, Secale, Sorghum, Triticale, Triticum, Zea.*

However, the use of the active compounds according to the invention is in no way restricted to these genera but extends in the same manner to other plants.

Depending on the concentration, the active compounds according to the invention are suitable for nonselective weed control, for example on industrial terrains and rail tracks, and on paths and areas with or without tree stands. Equally, the active compounds according to the invention can be employed for controlling weeds in perennial crops, for example forests, ornamental tree plantings, orchards, vineyards, citrus groves' nut orchards, banana plantations, coffee plantations, tea plantations, rubber plantations, oil palm plantations, cocoa plantations, soft fruit plantings and hop fields, in lawns, turf and pastures, and for the selective weed control in annual crops.

The compounds of the formula (I) according to the invention show a potent herbicidal activity and a broad spectrum of action when applied to the soil and to aerial plant parts. To a certain extent, they are also suitable for the selective control of monocotyledenous and dicotyledenous weeds in monocotyledenous and dicotyledenous crops, both by the pre-emergence and the post-emergence methods.

At certain concentrations or rates, the active compounds according to the invention can also be used for controlling animal pests and fungal or bacterial plant diseases. If appropriate, they can also be used as intermediates or precursors for the synthesis of further active ingredients.

All plants and plant parts can be treated in accordance with the invention. Plants are to be understood as meaning in the present context plants and plant populations such as desired and undesired wild plants or crop plants (inclusive of naturally occurring crop plants). Crop plants can be plants which can be obtained by conventional plant breeding and optimization methods or by biotechnological and recombinant methods or combinations of these methods, inclusive of the transgenic plants and inclusive of the plant varieties protectable or not protectable by Plant Breeders' Rights. Plant parts are to be understood as meaning all aerial and subterranean plant parts and organs of the plants such as shoot, leaf, flower and root, examples which may be mentioned being leaves, needles, stalks, stems, flowers, fruiting bodies, fruits, seeds, roots, tubers and rhizomes. The plant parts also include harvested goods and vegetative and generative propagation materials, for example cuttings, tubers, rhizomes, offsets and seeds.

The treatment according to the invention of the plants and plant parts with the active compounds is carried out directly or by allowing the compounds to act on their, surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations such as solutions, emulsions, wettable powders, suspensions, powders, dusts, pastes, soluble powders, granules, suspo-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is emulsifiers and/or dispersants and/or foam formers.

If the extender used is water it is also possible to use, for examples, organic solvent as cosolvents. Suitable liquid solvents are essentially: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example mineral oil-fractions, mineral or vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are: for example ammonium salts and ground natural minerals such as kaolins, clays, talc, chalk, quartz, attapulgite, montmorillonite or diatomaceous earth, and ground synthetic minerals such as highly-disperse silica, alumina and silicates; suitable solid carriers for granules are: for example crushed and fractionated natural rocks such as calcite, marble, pumice, sepiolite and dolomite, or else synthetic granules of inorganic and organic mills, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example ligno sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide, and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention, as such or in their formulations, can also be applied for weed control as a mixture with known herbicides and/or with materials which improve crop plant tolerance (safeners), readymixes and tank mixes being possible. Thus, mixtures with weed killers which contain one or more known herbicides and a safener are also possible.

Suitable herbicides for the mixtures are known herbicides, for example acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, beflubutamid, benazolin (-ethyl), benfuresate, bensulfuron (-methyl), bentazon, benzfendizone, benzobicyclon, benzofenap, benzoylprop (-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlomitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, di-allate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flufenpyr, flumetsulam, flumiclorac (-pentyl), flumioxazin, flumipropyne, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), bexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, ketospiradox, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, napropamide, naproanilide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, penoxysulam, pentoxazone, pethoxamid, phenmedipham, picolinafen, piperophos, pretilachlor, primisulfuron (-methyl), profluazol, profoxydim, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyrihuticarb, pyridate, pyridatol, pyriftalid, pyriminobac (-methyl), pyrithiobac (-sodium), quinchlorac, quinmerac, quinoclamine, quizalofop (-P-ethyl,-P-tefuryl), rimsulfuron, sethoxydim, simazine, simetryn, sulcotrione, sulfentrazone, sulfometuron (-methyl), sulfosate, sulfosulphuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, tri-allate, triasulfuron, tribenuron (-methyl), triclopyr, tridiphane, trifluralin, trifloxysulfuron, triflusulfuron (-methyl), tritosulfuron.

Also suitable for the mixtures are known safeners, for example AD-67, BAS-145138, benoxacor, cloquintocet (-mexyl), cyometrinil, 2,4-D, DKA-24, dichlormid, dymron, fenclorim, fenchloazol (-ethyl), flurazole, fluxofenim, furilazole, isoxadifen (-ethyl), MCPA, mecoprop (-P), mefenpyr (-diethyl), MG-191, oxabetrinil, PPG-1292, R-29148.

A mixture with other known active compounds such as fungicides, insecticides, acaricides, nematicides, bird repellents, plant nutrients and soil conditioners is also possible.

The active compounds can be applied as such, in the form of their formulations or the use forms prepared therefrom by further dilution, such as ready-to-use solutions, suspensions, emulsions, powders, pastes and granules. They are applied in the customary fashion, for example by pouring, spraying, atomizing, scattering.

The active compounds according to the invention can be applied both before and after emergence of the plants. They can also be incorporated into the soil before sowing.

The amount of active compound applied can vary within a substantial range. It depends essentially on the nature of the desired effect. In general, the application rates are between 1 g and 10 kg of active compound per hectare of soil surface, preferably between 5 g and 5 kg per ha.

As already mentioned above, all plants and their parts may be treated in accordance with the invention. In a preferred embodiment, plant species and plant varieties which grow in the wild or which have been obtained by conventional biological breeding methods, such as hybridization or protoplast fusion, and parts of these plant species and plant varieties are treated. In a further preferred embodiment, transgenic plants and plant varieties which have been obtained by genetic engineering methods, if appropriate in combination with conventional methods (genetically modified organisms) and parts of these plants and plant varieties are treated. The term "parts" or "parts of plants" or "plant parts" has been illustrated above.

Plants of the varieties which are commercially available or in use are especially preferably treated. Plant varieties are to be understood as meaning plants with certain traits which have been obtained both by conventional breeding, by mutagenesis or by recombinant DNA techniques. They can take the form of varieties, biotypes and genotypes.

Depending on the plant species or plant varieties, their location and growth conditions (soils, climate, vegetation period, nutrition) superadditive ("synergistic") effects may also occur as a result of the treatment in accordance with the invention. Thus, for example, reduced application rates and/or a widened spectrum of action and/or increased action of the substances and compositions which can be used according to the invention—also in combination with other agrochemical active compounds—, better crop plant growth, increased tolerance of crop plants to high or low temperatures, increased tolerance of the crop plants to drought or to water or soil salinity, increased flowering performance, facilitated harvesting, accelerated maturation, higher yields, higher quality and/or higher nutritional value of the harvested products, better shelf-life and/or processability of the harvested products are possible, which exceed the actual effects to be expected.

The preferred transgenic plants or plant varieties (obtained by genetic engineering) to be treated in accordance with the invention include all plants which, owing to modification by recombinant means, were provided with genetic material which imparts particular advantageous valuable traits to these plants. Examples of such properties are better plant growth, increased tolerance to high or low temperatures, increased tolerance to drought or to water or soil salinity, increased flowering performance, facilitated harvesting, accelerated maturation, higher yields, higher quality and/or higher nutritional value of the harvested products, greater shelf-life and/or processability of the harvested products. Other, especially emphasized: examples of such traits are an increased defence of the plants against animal and microbial pests such as to insects, mites, phytopathogenic fungi, bacteria and/or viruses, and an increased tolerance of the plants to certain herbicidal active compounds. Examples of transgenic plants which may be mentioned are important crop plants such as cereals (wheat, rice), maize, soya, potatoes, cotton, oilseed rape and fruit species (with the fruits apples, pears, citrus fruit and grapes), with particular emphasis being placed on maize, soya, potato, cotton and oilseed rape. Traits which are particularly emphasized are the increased defence of the plants against insects by toxins formed in the plants, in particular those which are generated by genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations) in the plants (hereinbelow "Bt plants"). Other traits which are particularly emphasized are the increased defence of plants against fungi, bacteria and viruses by systemic acquired resistance (SAR), systemin, phytoalexins, elicitors and resistance genes and correspondingly expressed proteins and toxins. Other traits which are particularly emphasized are the increased tolerance of the plants to certain herbicidal active compounds, for example imidazolinones, sulphonyl ureas, glyphosate or phosphinothricin (for example "PAT" gene). The genes which impart, each of the desired traits may also occur in combinations with each other in the transgenic plants. Examples of "Bt plants" which may be mentioned are varieties of maize, cotton, soya and potatoes, which are commercially available under the trade names YIELD GARD® (for example maize, cotton, soya), Knockout® (for example maize), StarLink® (for example maize), Boilgard® (cotton), Nucotn® (cotton) and NewLeaf® (potato). Examples of herbicide-tolerant plants which may be mentioned are varieties of maize, cotton and soya which are commercially available under the trade names Roundup Ready® (tolerance to glyphosate, for example maize, cotton, soya), Liberty Link® (tolerance to phosphinothricin, for example oilseed rape), IMI® (tolerance to imidazolinones) and STS® (tolerance to sulphonylureas, for example maize). Herbicide-resistant plants (plants bred conventionally for herbicide tolerance) which may also be mentioned are the varieties which are commercially available under the name Clearfield® (for example maize). Naturally, these statements also apply to plant varieties which will be developed in the future or which will be marketed in the future and which have these genetic traits, or genetic traits to be developed in the future.

The plants stated can be treated particularly advantageously in accordance with the invention with the compounds of the general formula I or the active compound mixtures according to the invention, the abovementioned synergistic effects with the transgenic plants or plant varieties being observed in addition to the good control of the weed plants. The preferred ranges stated above for the active compounds or mixtures also apply to the treatment of these plants. The treatment of plants with the compounds or mixtures specifically stated in the present text may be particularly emphasized.

The preparation and use of the active compounds according to the invention are illustrated by the examples which follow.

PREPARATION EXAMPLES

Example 1

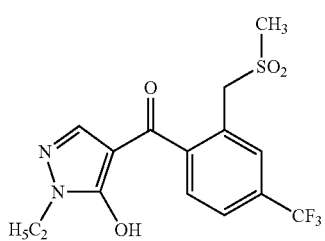

A mixture of 3.50 g (12.4 mmol) of 2-methylsulphonylmethyl-4-trifluoromethylbenzoic acid, 1.39 g (12.4 mmol) of 1-ethyl-5-hydroxy-1H-pyrazole, 3.07 g (14.9 mmol) of dicyclohexylcarbodiimide and 75 ml of acetonitrile is stirred at room temperature (about 20° C.) for 15 hours. 3.45 ml of triethylamine and 0.35 ml of trimethylsilyl cyanide are then added to this mixture, and the reaction mixture is stirred at room temperature for 15 hours. The mixture is then concentrated under reduced pressure and the residue is stirred with saturated aqueous sodium carbonate esolution, diethyl ether is added and the mixture is filtered. The aqueous phase of the filtrate is separated off, acifidied with 2N hydrochloric acid and extracted with methylene chloride. The organic extract solution is washed with water, dried with sodium sulphate and filtered. The filtrate is concentrated un der reduced pressure, the residue is digested with diethyl ether/petroleum ether and the resulting crystalline product is isolated by filtration with suction.

This gives 3.8 g (81.5% of theory) of (1-ethyl-5-hydroxy-1H-pyrazol-4-yl)-(2-methylsulphonylmethyl-4-trifluoromethylphenyl)methanone. Log P=1.88.

Example 2

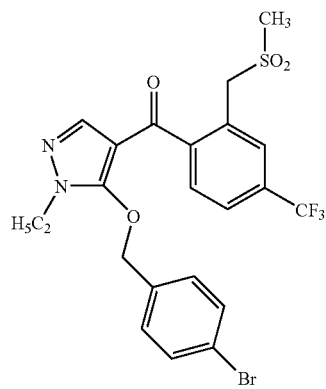

A mixture of 1.00 g (2.66 mmol) of (1-ethyl-5-hydroxy-1H-pyrazol-4-yl)-(2-methylsulphonylmethyl-4-trifluoromethylphenyl)methanone, 0.66 g (2.66 mmol) 4-bromobenzylbromide, 0.485 g of 1,8-diazabicyclo[5.4.0]undec-7-ene (DBU) and 50 ml of toluene is, with stirring, heated at reflux for 2 hours and then concentrated under reduced pressure. The residue is shaken with 2 N hydrochloric acid/ethyl acetate and the organic phase is dried with sodium sulphate and filtered. The filtrate is concentrated under reduced pressure, the residue is digested with hexane/diethyl ether/isopropanol and the resulting crystalline product is isolated by filtration with suction.

This gives 0.55 g (38% of theory) of [1-ethyl-5-(4-bromophenylmethoxy)-1H-pyrazol-4-yl]-(2-methylsulphonylmethyl-4-trifluoromethylphenyl)methanone. Log P=3.76.

Analogously to Examples 1 and 2, and in accordnace with the general description of the preparation process according to the invention, it is also possible to prepare, for example, the compounds of the general formula (I) listed in Tables 1 and 2 below.

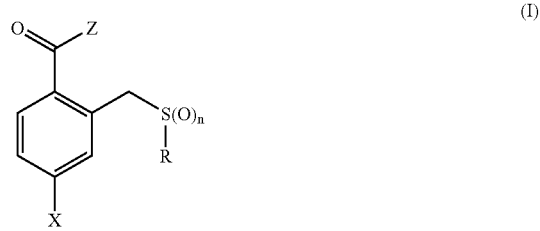

(I)

TABLE 1

| Ex. No. | n | R | X | Z | Physical Data |
|---|---|---|---|---|---|
| 1 | 2 | CH$_3$ | CF$_3$ | ![pyrazole with H$_5$C$_2$-N and OH] | logP = 1.88[a)] |

TABLE 1-continued

| Ex. No. | n | R | X | Z | Physical Data |
|---|---|---|---|---|---|
| 2 | 2 | CH₃ | CF₃ | 4-methyl-1-ethyl-5-(4-bromobenzyloxy)pyrazole | logP = 3.76[a] |
| 3 | 2 | CH₃ | CF₃ | 2-methylcyclohexane-1,3-dione | logP = 2.17[a] |
| 4 | 2 | CH₃ | CF₃ | 1,4-dimethyl-5-hydroxypyrazole | logP = 1.57[a] |
| 5 | 2 | CH₃ | CF₃ | 1,4-dimethyl-5-(benzyloxy)pyrazole | logP = 2.94[a] |
| 6 | 2 | CH₃ | CF₃ | 1,4-dimethyl-5-(4-fluorobenzyloxy)pyrazole | logP = 3.02[a] |
| 7 | 2 | CH₃ | CF₃ | 1,4-dimethyl-5-(4-chlorobenzyloxy)pyrazole | logP = 3.32[a] |
| 8 | 2 | CH₃ | CF₃ | 1,4-dimethyl-5-(4-bromobenzyloxy)pyrazole | logP = 3.41[a] |
| 9 | 2 | CH₃ | CF₃ | 1,4-dimethyl-5-(4-methylbenzyloxy)pyrazole | logP = 3.26[a] |
| 10 | 2 | CH₃ | CF₃ | 4-methyl-1-ethyl-5-(4-chlorobenzyloxy)pyrazole | logP = 3.64[a] |

TABLE 1-continued
| Ex. No. | n | R | X | Z | Physical Data |
|---|---|---|---|---|---|
| 11 | 2 | CH₃ | CF₃ | 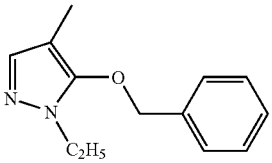 | logP = 3.26[a) |
| 12 | 2 | CH₃ | CF₃ | 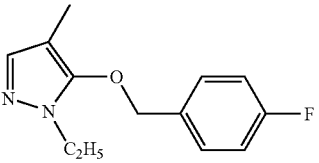 | logP = 3.30[a) |
| 13 | 2 | CH₃ | CF₃ | 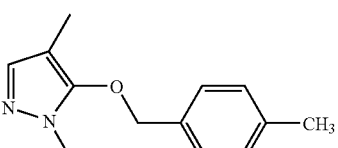 | logP = 3.57[a) |
| 14 | 2 | CH₃ | CF₃ | 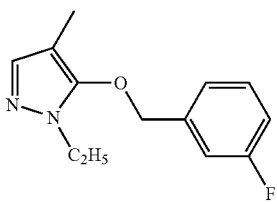 | logP = 3.30[a) |
| 15 | 2 | CH₃ | CF₃ | 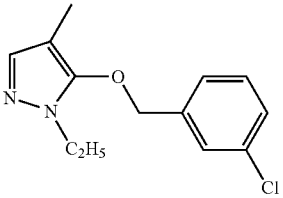 | logP = 3.60[a) |
| 16 | 2 | CH₃ | CF₃ | 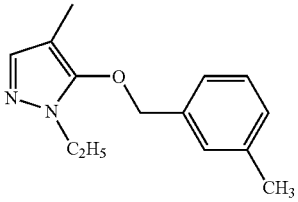 | logP = 3.57[a) |
| 17 | 2 | CH₃ | CF₃ | 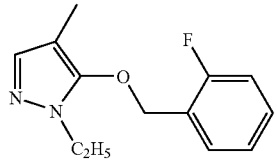 | logP = 3.29[a) |
| 18 | 2 | CH₃ | CF₃ | 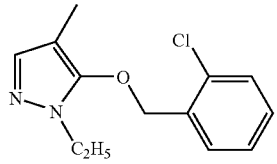 | logP = 3.56[a) |

TABLE 1-continued

| Ex. No. | n | R | X | Z | Physical Data |
|---|---|---|---|---|---|
| 19 | 2 | CH$_3$ | CF$_3$ | | logP = 3.52[a)] |
| 20 | 2 | CH$_3$ | CF$_3$ | | logP = 3.01[a)] |
| 21 | 2 | CH$_3$ | CF$_3$ | | logP = 3.07[a)] |
| 22 | 2 | CH$_3$ | CF$_3$ | | logP = 3.39[a)] |
| 23 | 2 | CH$_3$ | CF$_3$ | | logP = 2.50[a)] |
| 24 | 2 | CH$_3$ | CF$_3$ | | logP = 2.59[a)] |
| 25 | 2 | CH$_3$ | CF$_3$ | | logP = 2.72[a)] |
| 26 | 2 | CH$_3$ | CF$_3$ | | logP = 3.01[a)] |

TABLE 1-continued

| Ex. No. | n | R | X | Z | Physical Data |
|---|---|---|---|---|---|
| 27 | 2 | CH$_3$ | CF$_3$ | (1,4-dimethyl-pyrazol-5-yloxy)acetic acid ethyl ester | logP = 2.44[a)] |
| 28 | 2 | CH$_3$ | CF$_3$ | 2-(1,4-dimethyl-pyrazol-5-yloxy)propionic acid ethyl ester | logP = 2.70[a)] |
| 29 | 2 | CH$_3$ | CF$_3$ | 1,4-dimethyl-5-(prop-2-ynyloxy)-pyrazole | logP = 2.30[a)] |
| 30 | 2 | CH$_3$ | CF$_3$ | 2,4,4-trimethylcyclohexane-1,3-dione | logP = 2.86[a)] |
| 31 | 0 | C$_2$H$_5$ | CF$_3$ | 2-methylcyclohexane-1,3-dione | logP = 3.70[a)] |
| 32 | 0 | C$_2$H$_5$ | CF$_3$ | 1-ethyl-5-hydroxy-4-methylpyrazole | logP = 3.36[a)] |
| 33 | 2 | CH$_3$ | CF$_3$ | 3-chloro-2-methylcyclohex-2-enone | logP = 2.42[a)] |
| 34 | 2 | CH$_3$ | CF$_3$ | 2-methyl-3-(pyrazol-1-yl)cyclohex-2-enone | logP = 2.17[a)] |

TABLE 2

| Ex. No. | Structure | Physical Data |
|---|---|---|
| 35 | cyclohexane-1,3-dione-2-yl benzoyl with 2-CH2SCH3, 4-CF3 | 3.65 ppm |
| 36 | cyclohexane-1,3-dione-2-yl benzoyl with 2-CH2S(O)2CH2CH3, 4-CF3 | 4.39 ppm |
| 37 | cyclohexane-1,3-dione-2-yl benzoyl with 2-CH2S(O)2CH2CH2CH3, 4-CF3 | 154° C. |
| 38 | cyclohexane-1,3-dione-2-yl benzoyl with 2-CH2S(O)2CH2CH(CH3)2, 4-CF3 | 172° C. |
| 39 | 5,5-dimethyl-cyclohexane-1,3-dione-2-yl benzoyl with 2-CH2SO2CH3, 4-CF3 | 3.70 ppm |
| 40 | 5,5-dimethyl-cyclohexane-1,3-dione-2-yl benzoyl with 2-CH2SCH3, 4-CF3 | 4.40 ppm |
| 41 | 4,4-dimethyl-cyclohexane-1,3-dione-2-yl benzoyl with 2-CH2SCH3, 4-CF3 | 3.70 ppm |
| 42 | cyclohexane-1,3-dione-2-yl benzoyl with 2-CH2SO2CH3, 4-Br | 173.5° C. |
| 43 | cyclohexane-1,3-dione-2-yl benzoyl with 2-CH2SCH3, 4-Br | 3.62 ppm |
| 44 | cyclohexane-1,3-dione-2-yl benzoyl with 2-CH2SCH2CH3, 4-Br | 3.65 ppm |
| 45 | cyclohexane-1,3-dione-2-yl benzoyl with 2-CH2S(O)2CH2CH3, 4-Br | 4.30 ppm |
| 46 | cyclohexane-1,3-dione-2-yl benzoyl with 2-CH2SCH2CF3, 4-Br | 3.80 ppm |

TABLE 2-continued

| Ex. No. | Structure | Physical Data |
|---|---|---|
| 47 | 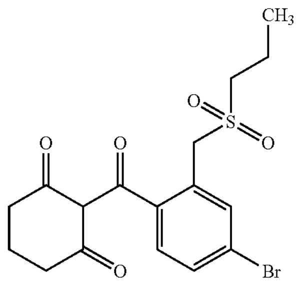 | 197° C. |
| 48 | 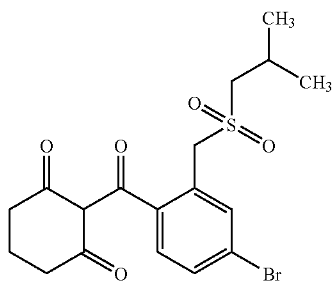 | 179 to 181° C. |
| 49 | 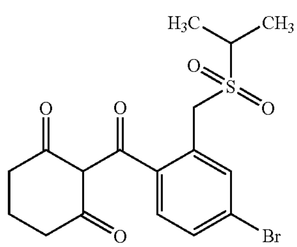 | 4.30 ppm |
| 50 | 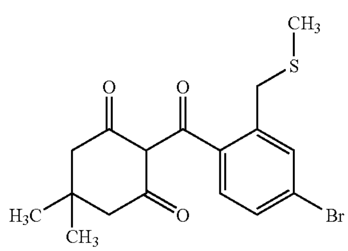 | 3.62 ppm |
| 51 | 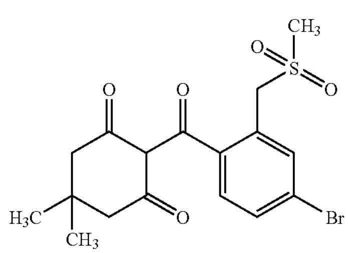 | 154° C. |
| 52 | 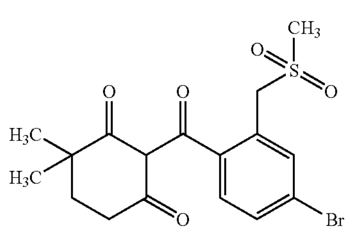 | 4.30 ppm |
| 53 | | 3.62 ppm |
| 54 | | 3.80 ppm |
| 56 | | 3.80 ppm |
| 57 | | 173.5° C. |
| 58 | | 76.5° C. |
| 59 | | 78° C. |

TABLE 2-continued

| Ex. No. | Structure | Physical Data |
|---|---|---|
| 60 | (3-methyl-5-hydroxy-1-methyl-pyrazol-4-yl)(2-(isobutylsulfonylmethyl)-4-trifluoromethylphenyl)methanone | 60.9° C. |
| 61 | (3-methyl-1-methyl-5-(phenacyloxy)pyrazol-4-yl)(2-(methylsulfonylmethyl)-4-trifluoromethylphenyl)methanone | 4.80 ppm |
| 62 | (3-methyl-1-methyl-5-(n-propylsulfonyloxy)pyrazol-4-yl)(2-(methylsulfonylmethyl)-4-trifluoromethylphenyl)methanone | 4.62 ppm |
| 63 | (3-methyl-1-methyl-5-(2,6-difluorobenzyloxy)pyrazol-4-yl)(2-(methylsulfonylmethyl)-4-trifluoromethylphenyl)methanone | 4.80 ppm |
| 64 | (3-methyl-1-methyl-5-(4-trifluoromethylbenzyloxy)pyrazol-4-yl)(2-(methylsulfonylmethyl)-4-trifluoromethylphenyl)methanone | 4.80 ppm |
| 65 | (3-methyl-5-hydroxy-1-methyl-pyrazol-4-yl)(2-(n-propylsulfonylmethyl)-4-trifluoromethylphenyl)methanone | 65° C. |
| 66 | (1-methyl-5-(n-propylsulfonyloxy)pyrazol-4-yl)(2-(methylsulfonylmethyl)-4-trifluoromethylphenyl)methanone | 4.60 ppm |
| 67 | (3-methyl-1-methyl-5-(n-propylsulfonyloxy)pyrazol-4-yl)(2-(n-propylsulfonylmethyl)-4-trifluoromethylphenyl)methanone | 4.60 ppm |
| 68 | (3-methyl-1-methyl-5-(phenacyloxy)pyrazol-4-yl)(2-(n-propylsulfonylmethyl)-4-trifluoromethylphenyl)methanone | 4.70 ppm |

TABLE 2-continued

| Ex. No. | Structure | Physical Data |
|---|---|---|
| 69 | 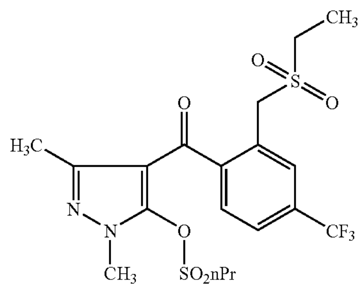 | 4.60 ppm |
| 70 | 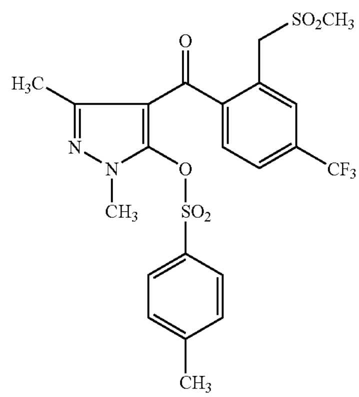 | 175° C. |
| 71 | 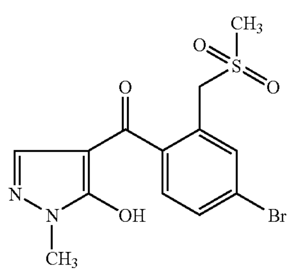 | 4.60 ppm |
| 72 | 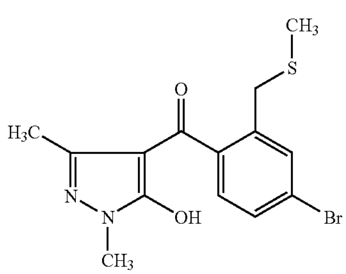 | 123° C. |
| 73 | 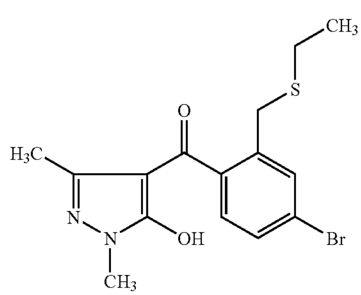 | 3.79 ppm |
| 74 | 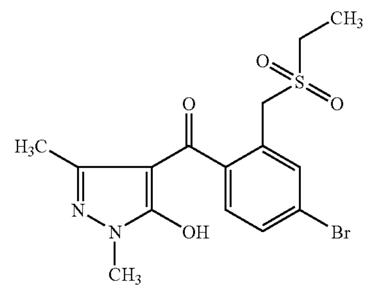 | 81° C. |
| 75 | 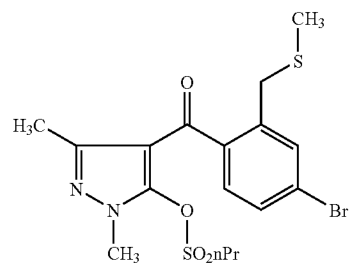 | 3.80 ppm |
| 76 | 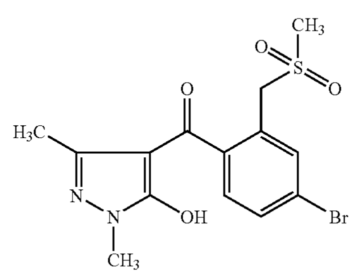 | 208° C. |
| 77 | 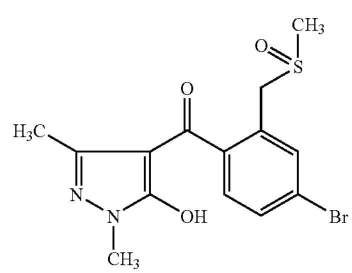 | 4.0/4.2 ppm |
| 78 | 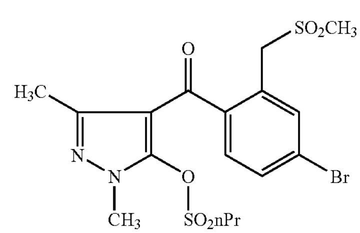 | 4.50 ppm |

TABLE 2-continued

| Ex. No. | Structure | Physical Data |
|---|---|---|
| 79 | | 3.90 ppm |
| 80 | | 4.60 ppm |
| 81 | | 44° C. |
| 82 | | 4.61 ppm |
| 83 | 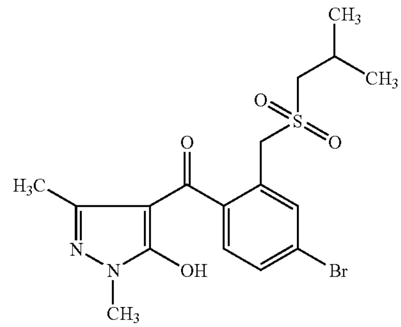 | 169° C. |
| 84 | 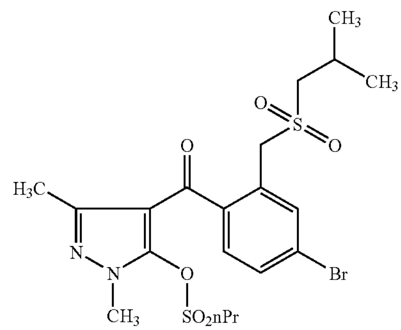 | 51° C. |
| 85 | 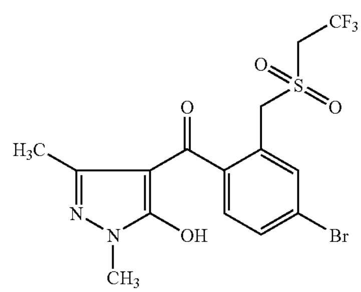 | 4.60 ppm |
| 86 | 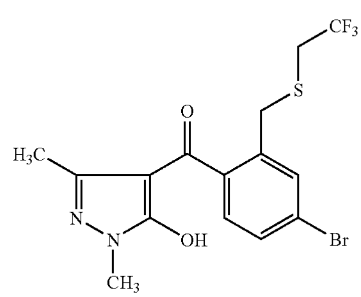 | 3.90 ppm |
| 87 | 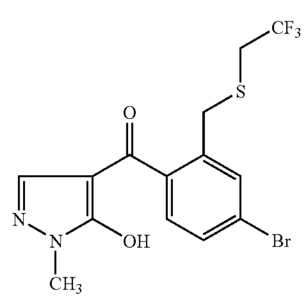 | 92° C. |

TABLE 2-continued

| Ex. No. | Structure | Physical Data |
|---|---|---|
| 88 | | 180° C. |
| 89 | | 201° C. |
| 90 | | 4.59 ppm |
| 91 | | |
| 92 | | |
| 93 | 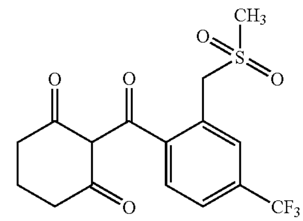 | |
| 94 | 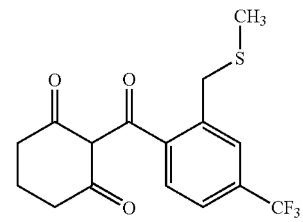 | |
| 95 | 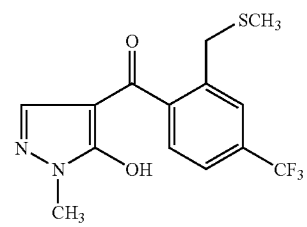 | 100° C. |
| 96 | 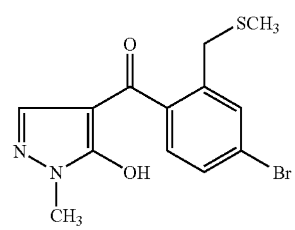 | 85° C. |
| 97 | 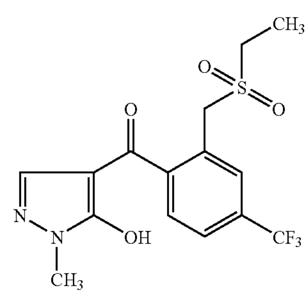 | 186° C. |
| 98 | 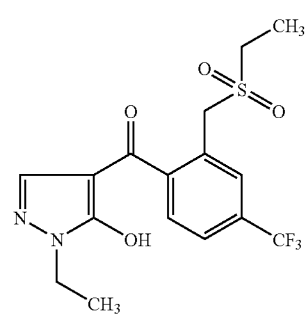 | 4.65 ppm |

TABLE 2-continued

| Ex. No. | Structure | Physical Data |
|---|---|---|
| 99 | 3-methyl-1-methyl-5-(prop-2-yn-1-yloxy)-1H-pyrazol-4-yl 2-(methylsulfonylmethyl)-4-(trifluoromethyl)phenyl ketone | |
| 100 | 3-methyl-1-methyl-5-(prop-2-yn-1-yloxy)-1H-pyrazol-4-yl 4-bromo-2-(methylsulfonylmethyl)phenyl ketone | |
| 101 | 1-methyl-5-(prop-2-yn-1-yloxy)-1H-pyrazol-4-yl 4-bromo-2-(methylsulfonylmethyl)phenyl ketone | 4.47 ppm |
| 102 | 3-methyl-5-hydroxy-1-methyl-1H-pyrazol-4-yl 2-(methylsulfonylmethyl)-4-(methylsulfonyl)phenyl ketone | |
| 103 | 3-methyl-5-hydroxy-1-methyl-1H-pyrazol-4-yl 2-(methylthiomethyl)-4-(methylsulfonyl)phenyl ketone | |
| 104 | 5-hydroxy-1-methyl-1H-pyrazol-4-yl 2-(methylthiomethyl)-4-(methylsulfonyl)phenyl ketone | |
| 105 | 5-hydroxy-1-methyl-1H-pyrazol-4-yl 2-(methylsulfonylmethyl)-4-(methylsulfonyl)phenyl ketone | |
| 106 | 3-methyl-5-hydroxy-1-methyl-1H-pyrazol-4-yl 2-(methylthiomethyl)-4-(trifluoromethoxy)phenyl ketone | |
| 107 | 3-methyl-5-hydroxy-1-methyl-1H-pyrazol-4-yl 2-(methylsulfonylmethyl)-4-(trifluoromethoxy)phenyl ketone | |
| 108 | 5-hydroxy-1-methyl-1H-pyrazol-4-yl 2-(methylthiomethyl)-4-(trifluoromethoxy)phenyl ketone | |
| 109 | 5-hydroxy-1-methyl-1H-pyrazol-4-yl 2-(methylsulfonylmethyl)-4-(trifluoromethoxy)phenyl ketone | |
| 110 | 2-[2-(methylthiomethyl)-4-(methylthio)benzoyl]cyclohexane-1,3-dione | |

TABLE 2-continued

| Ex. No. | Structure | Physical Data |
|---|---|---|
| 111 | 1-methyl-5-hydroxy-pyrazol-4-yl 2-(ethylthiomethyl)-4-(trifluoromethyl)phenyl ketone | |
| 112 | 1-ethyl-5-(n-propylsulfonyloxy)-pyrazol-4-yl 2-(methylsulfonylmethyl)-4-bromophenyl ketone | 4.80 ppm |
| 113 | 1-ethyl-5-hydroxy-pyrazol-4-yl 2-(methylthiomethyl)-4-(trifluoromethyl)phenyl ketone | |
| 114 | 1-ethyl-5-hydroxy-pyrazol-4-yl 2-(methylthiomethyl)-4-bromophenyl ketone | |
| 115 | 1-methyl-5-hydroxy-pyrazol-4-yl 2-(methylthiomethyl)-4-(methylthio)phenyl ketone | |
| 116 | 1,3-dimethyl-5-hydroxy-pyrazol-4-yl 2-(methylthiomethyl)-4-(methylthio)phenyl ketone | |
| 117 | 1-ethyl-5-hydroxy-pyrazol-4-yl 2-(methylthiomethyl)-4-(methylthio)phenyl ketone | |
| 118 | 1-methyl-5-(n-propylsulfonyloxy)-pyrazol-4-yl 2-(methylsulfonylmethyl)-4-(methylsulfonyl)phenyl ketone | |
| 119 | 1,3-dimethyl-5-(n-propylsulfonyloxy)-pyrazol-4-yl 2-(methylsulfonylmethyl)-4-(methylsulfonyl)phenyl ketone | |
| 120 | 1-ethyl-5-(n-propylsulfonyloxy)-pyrazol-4-yl 2-(methylsulfonylmethyl)-4-(methylsulfonyl)phenyl ketone | |
| 121 | 1-ethyl-5-hydroxy-pyrazol-4-yl 2-(methylsulfonylmethyl)-4-iodophenyl ketone | |

TABLE 2-continued

| Ex. No. | Structure | Physical Data |
|---|---|---|
| 122 | 1-ethyl-5-hydroxy-pyrazol-4-yl (4-bromo-2-(methylsulfonylmethyl)phenyl) ketone | |
| 123 | 1-ethyl-5-hydroxy-pyrazol-4-yl (4-fluoro-2-(methylsulfonylmethyl)phenyl) ketone | |
| 124 | 2-(4-iodo-2-(methylsulfonylmethyl)benzoyl)cyclohexane-1,3-dione | |
| 125 | 2-(4-bromo-2-(methylsulfonylmethyl)benzoyl)cyclohexane-1,3-dione | |
| 126 | 2-(4-fluoro-2-(methylsulfonylmethyl)benzoyl)cyclohexane-1,3-dione | |
| 127 | 1,3-dimethyl-5-hydroxy-pyrazol-4-yl (4-iodo-2-(methylsulfonylmethyl)phenyl) ketone | |
| 128 | 1,3-dimethyl-5-hydroxy-pyrazol-4-yl (4-fluoro-2-(methylsulfonylmethyl)phenyl) ketone | |
| 129 | 1-methyl-5-hydroxy-pyrazol-4-yl (4-iodo-2-(methylsulfonylmethyl)phenyl) ketone | |
| 130 | 1-methyl-5-hydroxy-pyrazol-4-yl (4-fluoro-2-(methylsulfonylmethyl)phenyl) ketone | |
| 131 | 1-methyl-5-hydroxy-pyrazol-4-yl (4-bromo-2-(methylsulfonylmethyl)phenyl) ketone | |
| 132 | 1,3-dimethyl-5-hydroxy-pyrazol-4-yl (4-bromo-2-(methylsulfonylmethyl)phenyl) ketone | |
| 133 | 1-methyl-5-(2-(4-trifluoromethylphenyl)-2-oxoethoxy)-pyrazol-4-yl (4-trifluoromethyl-2-(methylsulfonylmethyl)phenyl) ketone | |

TABLE 2-continued

| Ex. No. | Structure | Physical Data |
|---|---|---|
| 134 | | |
| 135 | | |
| 136 | | |
| 137 | | |
| 138 | 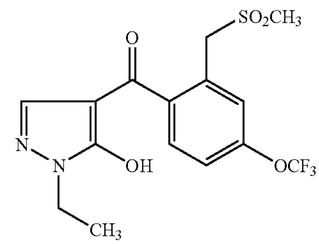 | |
| 139 | 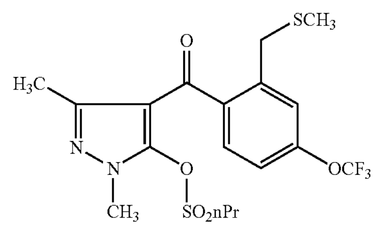 | |
| 140 | 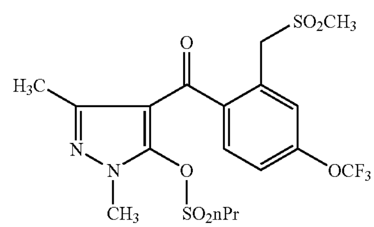 | |
| 141 | 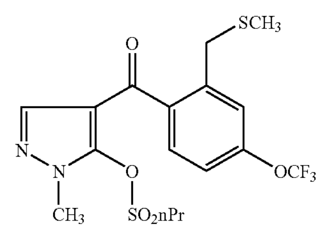 | |
| 142 | 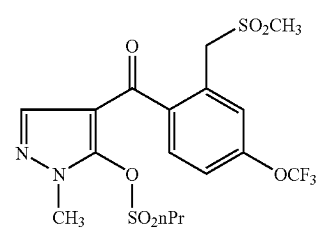 | |
| 143 | 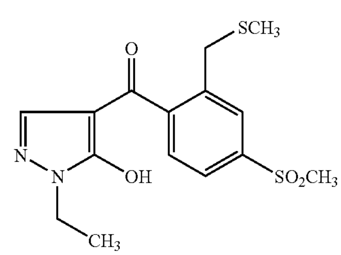 | |

TABLE 2-continued

| Ex. No. | Structure | Physical Data |
|---|---|---|
| 144 | 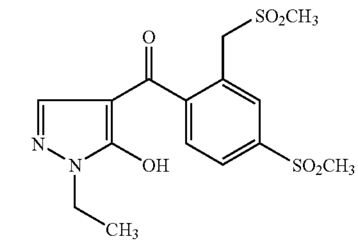 | |
| 145 | 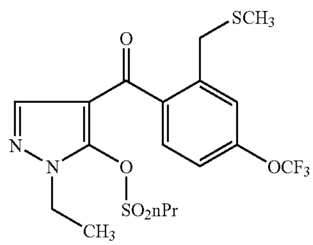 | |
| 146 | 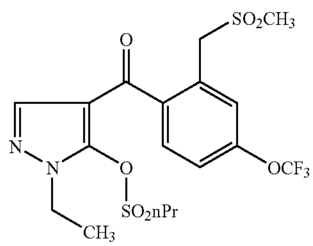 | |
| 147 | 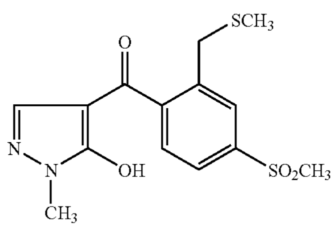 | |
| 148 | 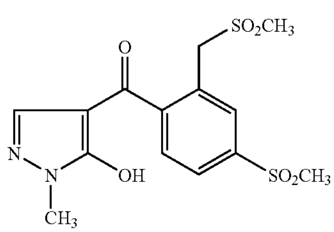 | |
| 149 | 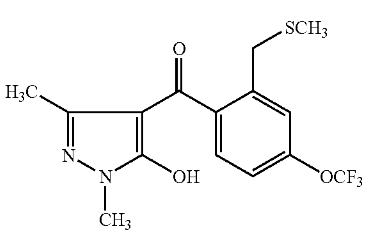 | |
| 150 | | |
| 151 | | |
| 152 | | |
| 153 | | |
| 154 | | |
| 155 | | |

TABLE 2-continued

| Ex. No. | Structure | Physical Data |
|---|---|---|
| 156 | 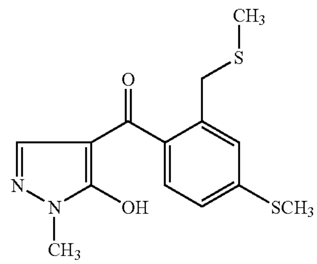 | |
| 157 | 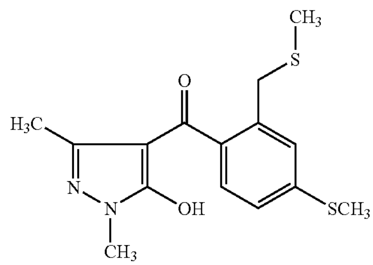 | |
| 158 | 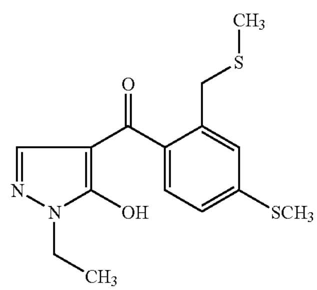 | |
| 159 | 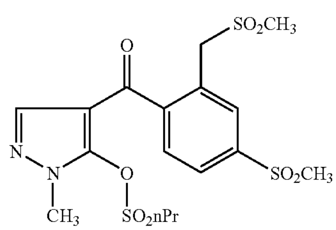 | |
| 160 | 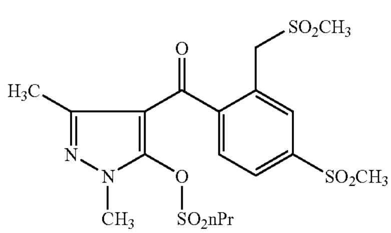 | |
| 161 | 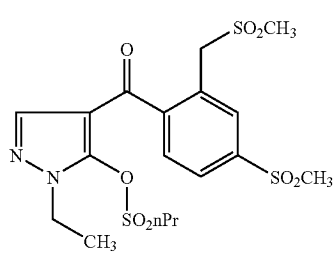 | |
| 162 | 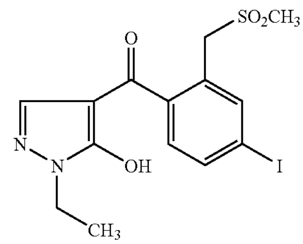 | |
| 163 | 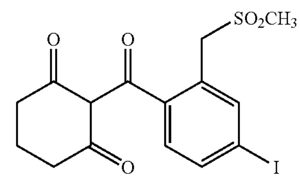 | |
| 164 | 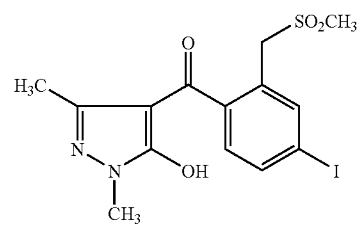 | |
| 165 | 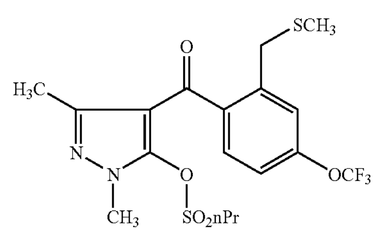 | |
| 166 | 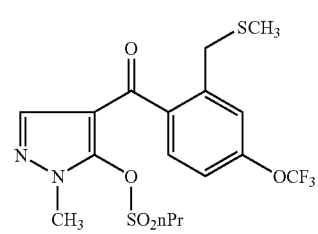 | |
| 167 | 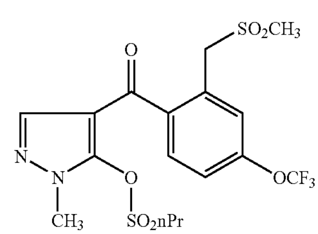 | |

TABLE 2-continued

| Ex. No. | Structure | Physical Data |
|---|---|---|
| 168 | 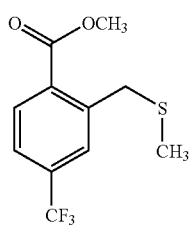 | |

Remarks for the column "physical data" of Tables 1 and 2: what is stated is either the logP value, the melting point or a characteristic NMR signal.

The logP values given in the tables were determined in accordance with EEC Directive 79/831 Annex V.A8 by HPLC (High Performance Liquid Chromatography) using a reverse-phase column (C 18). Temperature: 43° C.

(a) Mobile phases for the determination in the acidic range: 0.1% aqueous phosphoric acid, acetonitrile; linear gradient from 10% acetonitrile to 90% acetonitrile—corresponding measurement data are marked a) in Table 1.

(b) Mobile phases for the determination in the neutral range: 0.01 molar aqueous phosphate buffer solution, acetonitrile; linear gradient from 10% acetonitrile to 90% acetonitrile—the corresponding measurement data are marked b) in Table 1.

The calibration was carried out using unbranched alkan-2-ones (having 3 to 16 carbon atoms) with known logP values (determination of the logP values by the retention times using linear interpolation between two successive alkanones).

The lambda-max values were determined in the maxima of the chromatographic signals using the UV spectra from 200 nm to 400 nm.

The melting points given in the tables were determined by customary laboratory methods in capillary tubes for the melting point determination using a Melting point B-545 apparatus from Büchi. The melting point is stated in ° C.

The $^1$H-NMR data were determined in a 300 MHz apparatus using the solvent CDCl$_3$. What is stated is the characteristic signal of the CH$_2$ group between the central phenyl ring and the radical —S(O)$_n$R.

Starting Materials of the Formula (II):

Example (II-1)

Step 1

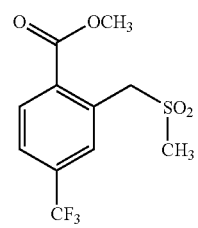

A mixture of 15 g (50.5 mmol) of methyl 2-bromomethyl-4-trifluoromethylbenzoate, 4.24 g (60.6 mmol) of sodium methyl mercaptide and 100 ml of acetonitnile is, with stirring, heated at reflux for 90 minutes. The mixture is then filtered off with suction through a silica gel frit, the residue is washed with petroleum ether and the solvent is carefully distilled off from the filtrate under reduced pressure.

This gives 12 g (90% of theory) of methyl 2-methylthiomethyl-4-trifluoromethylbenzoate.

Step 2

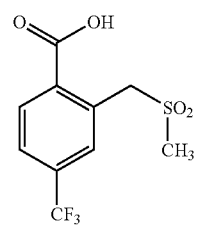

12.0 g (45.45 mmol) of methyl 2-methylthiomethyl-4-trifluoromethylbenzoate are taken up in 150 ml of acetic acid and, at room temperature, 10.2 g of a 35% strength aqueous hydrogen peroxide solution (0.10 mol of H$_2$O$_2$) are added dropwise with stirring. With stirring, the mixture is then heated at 100° C. for 90 minutes and then poured onto about twice the amount of ice. The resulting crystalline product is isolated by filtration with suction.

This gives 9.1 g (68% of theory) of methyl 2-methylsulphonylrhethyl-4-trifluoromethylbenzoate.

Step 3

A mixture of 9.0 g (30.4 mmol) of methyl 2-methylsulphonylmethyl-4-trifluoromethylbenzoate, 50 ml of 40% strength aqueous sodium hydroxide solution and 50 ml of water is heated at 90° C. for 60 minutes. After cooling, the mixture is diluted with water to about twice its volume and acidified with conc. hydrochloric acid, and the resulting crystalline product is isolated by filtration with suction.

This gives 7.15 g (83% of theory) of 2-methylsulphonyl-methyl-4-trifluoromethylbenzoic acid.

Use Examples

Example A

Pre-Emergence Test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen such that the particular amount of active compound desired is applied in 1000 liters of water per hectare.

After three Weeks, the degree of damage to the plants is rated in % damage in comparison to the development of the untreated control. The figures denote:

0%=no effect (like untreated control)
100%=total destruction

In this test, for example, the compounds of Preparation Examples 1, 2, 3, 4, 5, 6, 7, 8, 9, 10, 11, 12, 13, 14, 15, 16, 17, 18, 19, 20, 21, 22 and 23 exhibit strong activity against weeds, and some of them are tolerated well by crop plants, such as, for example, maize and soya beans.

Example B

Post-Emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated of amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor is chosen such that the particular amounts of active compound desired are applied in 1000 l of water/Ha.

After three weeks, the degree of damage to the plants is rated in % damage in comparison to the development of the untreated control.

The figures denote:
0%=no effect (like untreated control)
100%=total destruction In this test, for example, the compounds of Preparation Examples 1, 2, 3, 5, 18, 19, 20 and 23 exhibit strong activity against weeds, and some of them are tolerated well by crop plants, such as, for example, maize and wheat.

What is claimed is:

1. A herbicidal compound of formula (I),

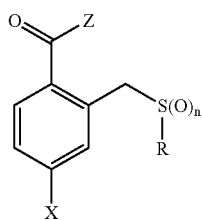

in which
n represents the number 0, 1, or 2,
R represents optionally substituted alkyl, alkenyl, alkynyl, cycloalkyl, cycloalkylalkyl, aryl, or arylalkyl,
X represent hydrogen, nitro, cyano, carboxy, carbamoyl, thiocarbamoyl, or halo; or represents optionally substituted alkyl, alkoxy, alkylthio, alkylsulphinyl, alkylsulphonyl, alkylamino, dialkylamino, or dialkylaminosulphonyl, and
Z represents one of the groups

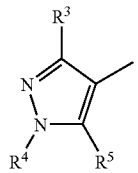

where
m represents the number 0 to 6,
R$^1$ represents hydrogen or halogen; or represents optionally substituted alkyl, alkylthio or aryl, with the proviso that if m represents the numbers 2 to 6, then R$^1$ together with a second radical R$^1$ optionally also represents oxygen or alkandiyl (alkylene),
R$^2$ represents hydroxyl, formyloxy, or halogen; represents optionally substituted alkoxy, alkylthio, alkylsulphinyl, alkylsulphonyl, alkylcarbonyloxy, alkoxycarbonyloxy, alkylaminocarbonyloxy, alkylsulphonyloxy, alkenyloxy, alkynyloxy, aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl, or arylalkylsulphonyl; or represents heterocyclyl that is attached via nitrogen,
R$^3$ represents cycloalkyl,
R$^4$ represents hydrogen; or represents optionally substituted alkyl, alkenyl, alkynyl, cycloalkyl, cycloalkylalkyl, aryl, or arylalkyl, and
R$^5$ represents hydroxyl or formyloxy; or represents optionally substituted alkoxy, alkylcarbonyloxy, alkoxycarbonyloxy, alkylaminocarbonyloxy, alkylsulphonyloxy, alkenyloxy, alkynyloxy, arylalkoxy, arylcarbonyloxy, arylcarbonylalkoxy, or arylsulphonyloxy.

2. A compound of formula (I) according to claim 1 in which
n represents the number 0 or 2,
R represents optionally cyano-, halogen-, $C_1$–$C_4$-alkoxy-, $C_1$–$C_4$-alkylthio-, $C_1$–$C_4$-alkylsulphinyl-, or $C_1$–$C_4$-alkylsulphonyl-substituted alkyl having 1 to 6 carbon atoms; represents optionally cyano- or halogen-substituted alkenyl or alkynyl having in each case 2 to 6 carbon atoms; represents optionally cyano-, halogen-, or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety; or represents optionally nitro-, cyano-, halogen-, $C_1$–$C_4$-alkyl-, $C_1$–$C_4$-haloalkyl-, $C_1$–$C_4$-alkoxy-, or $C_1$–$C_4$-haloalkoxy-substituted aryl or arylalkyl having in each case 6 or 10 carbon atoms in the aryl group and optionally 1 to 4 carbon atoms in the alkyl moiety,
X represents hydrogen, nitro, cyano, carboxyl, carbamoyl, thiocarbamoyl, or halogen; or represents optionally cyano-, halogen-, $C_1$–$C_4$-alkoxy-, $C_1$–$C_4$-alkylthio-, $C_1$–$C_4$-alkylsulphinyl-, or $C_1$–$C_4$-alkylsulphonyl-substituted alkyl, alkoxy, alkylthio, alkylsulphinyl, alkylsulphonyl, alkylamino, dialkylamino, or dialkylaminosulphonyl having in each case 1 to 6 carbon atoms in the alkyl groups, m represents the number 0, 1, 2, or 3, R¹ represents hydrogen or halogen; represents optionally cyano-, halogen-, $C_1$–$C_4$-alkoxy-, $C_1$–$C_4$-alkylthio-, $C_1$–$C_4$-alkylsulphinyl-, or $C_1$–$C_4$-alkylsulphonyl-substituted alkyl or alkylthio having in each case 1 to 6 carbon atoms; or represents phenyl, with the proviso that if m represents 2 or 3, then R¹ together with a second radical R¹ optionally also represents oxygen or alkanediyl (alkylene) having 3 to 5 carbon atoms, R² represents hydroxyl, formyloxy, or halogen; represents optionally cyano-, halogen-, $C_1$–$C_4$-alkyl-, $C_1$–$C_4$-alkoxy-carbonyl-, $C_1$–$C_4$-alkylthio-, $C_1$–$C_4$-alkylsulphinyl-, or $C_1$–$C_4$-alkylsulphonyl-substituted alkoxy, alkylthio, alkylsulphinyl, alkylsulphonyl, alkylcarbonyloxy, alkoxycarbonyloxy, alkylaminocarbonyloxy, or alkylsulphonyloxy having in each case 1 to 6 carbon atoms; represents optionally halogen-substituted alkenyloxy or alkynyloxy having in each case 3 to 6 carbon atoms; represents optionally nitro-, cyano-, halogen-, $C_1$–$C_4$-alkyl-, $C_1$–$C_4$-haloalkyl-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkylsulphinyl-, $C_1$–$C_4$-haloalkylsulphinyl-, $C_1$–$C_4$-alkylsulphonyl-, or $C_1$–$C_4$-haloalkylsulphonyl-substituted aryloxy, arylthio, arylsulphinyl, arylsulphonyl, arylcarbonyloxy, arylcarbonylalkoxy, arylsulphonyloxy, arylalkoxy, arylalkylthio, arylalkylsulphinyl, or arylalkylsulphonyl having in each case 6 or 10 carbon atoms in the aryl group and optionally 1 to 4 carbon atoms in the alkyl moiety; or represents pyrrolyl, pyrazolyl, imidazolyl, triazolyl, or tetrazolyl, each of which is attached via nitrogen, R³ represents optionally cyano-, halogen-, or $C_1$–$C_4$-alkyl-substituted cycloalkyl having 3 to 6 carbon atoms, R⁴ represents hydrogen; represents optionally cyano-halogen-, $C_1$–$C_4$-alkoxy-, $C_1$–$C_4$-alkyl-thio-, $C_1$–$C_4$-alkylsulphinyl-, or $C_1$–$C_4$-alkylsulphonyl-substituted alkyl having 1 to 6 carbon atoms; represents optionally cyano- or halogen-substituted alkenyl or alkynyl having in each case 3 to 6 carbon atoms; represents optionally cyano-, halogen-, or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety; or represents optionally nitro-, cyano-, halogen-, $C_1$–$C_4$-alkyl-, $C_1$–$C_4$-haloalkyl-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkylsulphinyl-, $C_1$–$C_4$-haloalkylsulphinyl-, $C_1$–$C_4$-alkylsulphonyl-, or $C_1$–$C_4$-haloalkylsulphonyl-substituted aryl or arylalkyl having in each case 6 or 10 carbon atoms in the aryl group and optionally 1 to 4 carbon atoms in the alkyl moiety, and R⁵ represents hydroxyl or formyloxy; represents optionally cyano-, halogen-, or $C_1$–$C_4$-alkoxy-substituted alkoxy, alkylcarbonyloxy, alkoxycarbonyloxy, alkylaminocarbonyloxy, or alkylsulphonyloxy having in each case 1 to 6 carbon atoms in the alkyl groups; represents optionally cyano- or halogen-substituted alkenyloxy or alkynyloxy having in each case 3 to 6 carbon atoms; or represents optionally nitro-, cyano-, halogen-, $C_1$–$C_4$-alkyl-, $C_1$–$C_4$-haloalkyl-, $C_1$–$C_4$-alkoxy-, $C_1$–$C_4$-haloalkoxy-, $C_1$–$C_4$-alkylthio-, $C_1$–$C_4$-haloalkylthio-, $C_1$–$C_4$-alkylsulphinyl-, $C_1$–$C_4$-haloalkylsulphinyl-, $C_1$–$C_4$-alkylsulphonyl-, or $C_1$–$C_4$-haloalkylsulphonyl-substituted arylalkoxy, arylcarbonyloxy, arylcarbonylalkoxy, or arylsulphonyloxy having in each case 6 or 10 carbon atoms in the aryl group and optionally 1 to 4 carbon atoms in the alkyl moiety.

3. A compound of formula (I) according to claim 1 in which n represents the number 2, R represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, n- or i-propylsulphinyl-, methylsulphonyl-, ethylsulphonyl- and/or n- or i-propylsulphonyl-substituted methyl, ethyl, n- or i-propyl, n-, i-, s-, or t-butyl, or n-, i-, s-, or t-pentyl; represents optionally cyano-, fluorine-, chlorine-, and/or bromine-substituted ethenyl, propenyl, butenyl, pentenyl, ethynyl, propynyl, butynyl, or pentynyl; represents optionally cyano-, fluorine-, chlorine-, bromine-, methyl-, ethyl-, and/or n- or i-propyl-substituted cyclopropyl, cyclobutyl, cyclopentyl, cyclohexyl, cyclopropylmethyl, cyclobutylmethyl, cyclopentylmethyl, or cyclohexylmethyl; or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, and/or trifluoromethoxy-substituted phenyl, naphthyl, phenylmethyl, phenylethyl, or phenylpropyl, X represents hydrogen, nitro, cyano, carboxyl, carbamoyl, thiocarbamoyl, fluorine, chlorine, bromine, or iodine; or represents optionally cyano-, fluorine-, chlorine-, methoxy-, ethoxy-, methylthio-, ethylthio-, methylsulphinyl-, ethylsulphinyl-, methylsulphonyl-, or ethylsulphonyl-substituted methyl, ethyl, n- or i-propyl, n-, i-, s-, or t-butyl, methoxy, ethoxy, n- or i-propoxy, n-, i-, s-, or t-butoxy, methylthio, ethylthio, n- or i-propylthio, n-, i-, s-, or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl, or diethylaminosulphonyl, m represents the number 0, 1, or 2, R¹ represents hydrogen, fluorine, chlorine, or bromine; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methyl, ethyl, n- or i-propyl, n-, i-, s-, or t-butyl, methylthio, ethylthio, n- or i-propylthio, or n-, i-, s-, or t-butylthio; or represents phenyl, with the proviso that if m represents 2, then R¹ together with a second radical R¹ optionally also represents oxygen, propane-1,3-diyl, or butane-1,4-diyl, R² represents hydroxyl, formyloxy, fluorine, or chlorine; represents optionally cyano-, fluorine-, chlorine-, methoxy-, ethoxy-, n- or i-propoxy-, methoxycarbonyl-, ethoxycarbonyl-, n- or i-propoxycarbonyl-, methylthio-, ethylthio-, n- or i-propylthio-, methylsulphinyl-, ethylsulphinyl-, methylsulphonyl-, or ethylsulphonyl-substituted methoxy, ethoxy, n- or i-propoxy, methylthio, ethylthio, n- or i-propylthio, methylsulphinyl, ethylsulphinyl, methylsulphonyl, ethylsulphonyl, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine-, chlorine-, and/or bromine-substituted propenyloxy, butenyloxy, propynyloxy, or butynyloxy; represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyloxy, phenylthio, phenylsulphinyl, phenylsulphonyl, phenylcarbonyloxy, phenylcarbonylmethoxy, phenylsulphonyloxy, phenylmethoxy, phenylmethylthio, phenylmethylsulphinyl, or phenylmethylsulphonyl; or represents pyrazolyl, imidazolyl, or triazolyl, each of which is attached via nitrogen, $R^3$ represents optionally cyano-, fluorine-, chlorine-, methyl-, or ethyl-substituted cyclopropyl, cyclobutyl, cyclopentyl, or cyclohexyl, $R^4$ represents hydrogen; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methyl, ethyl, n- or i-propyl, or n-, i-, s-, or t-butyl; represents optionally cyano-, fluorine-, chlorine-, and/or bromine-substituted propenyl, butenyl, propynyl, or butynyl; represents optionally cyano-, fluorine-, chlorine-, methyl-, or ethyl-substituted cyclopropyl, cyclobutyl, cyclopentyl, cyclohexyl, cyclopropylmethyl, cyclobutylmethyl, cyclopentylmethyl, or cyclohexylmethyl; or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyl or phenylmethyl, and $R^5$ represents hydroxyl or formyloxy; represents optionally cyano-, fluorine-, chlorine-, methoxy-, ethoxy-, n- or i-propoxy-substituted methoxy, ethoxy, n- or i-propoxy, acetyloxy, propionyloxy, n- or i-butyroyloxy, methoxy-carbonyloxy, ethoxycarbonyloxy, n- or i-propoxycarbonyloxy, methyl-aminocarbonyloxy, ethylaminocarbonyloxy, n- or i-propylaminocarbonyloxy, methylsulphonyloxy, ethylsulphonyloxy, or n- or i-propylsulphonyloxy; represents optionally cyano-, fluorine-, chlorine-, and/or bromine-substituted propenyloxy, butenyloxy, propynyloxy, or butynyloxy; or represents optionally nitro-, cyano-, fluorine-, chlorine-, bromine-, methyl-, ethyl-, n- or i-propyl-, n-, i-, s-, or t-butyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoro-methylsulphonyl-substituted phenylmethoxy, phenylcarbonyloxy, phenylcarbonylmethoxy, or phenylsulphonyloxy.

4. A compound of formula (I) according to claim 1 in which

R represents optionally fluorine- and/or chlorine-substituted methyl, ethyl, n- or i-propyl, or n-, i-, or s-butyl; represents optionally fluorine-, chlorine-, or methyl-substituted cyclopropyl, cyclopentyl, or cyclohexyl; or represents optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, or trifluoromethoxy-substituted phenyl or phenylmethyl, X represents nitro, cyano, carbamoyl, thiocarbamoyl, fluorine, chlorine, bromine, or iodine; or represents optionally fluorine-, chlorine-, methoxy-, ethoxy-, methylthio-, ethylthio-, methylsulphinyl-, ethylsulphinyl-, methylsulphonyl-, and/or ethylsulphonyl-substituted methyl, ethyl, methoxy, ethoxy, methylthio, ethylthio, methylsulphinyl, ethylsulphinyl, methylsulphonyl, ethylsulphonyl, dimethylamino, or dimethylaminosulphonyl, m represents the number 0, $R^1$ represents hydrogen; represents optionally fluorine- or chlorine-substituted methyl, ethyl, n- or i-propyl, methylthio, ethylthio, or n- or i-propylthio; or represents phenyl, with the proviso that if m represents 2, then $R^1$ together with a second radical $R^1$ optionally also represents oxygen, propane-1,3-diyl, or butane-1,4-diyl, $R^2$ represents hydroxyl; represents optionally fluorine- or chlorine-substituted methoxy, ethoxy, n- or i-propoxy, methoxycarbonyl, ethoxycarbonyl, n- or i-propoxycarbonyl, methylthio, ethylthio, n- or i-propylthio, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine-, chlorine-, and/or bromine-substituted propenyloxy, butenyloxy, propynyloxy, or butynyloxy; represents optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyloxy, phenylthio, phenylcarbonyloxy, phenylcarbonylmethoxy, phenylsulphonyloxy, phenylmethoxy, or phenylmethylthio; or represents pyrazolyl or imidazolyl, each of which is attached via nitrogen, $R^3$ represents optionally fluorine-, chlorine-, or methyl-substituted cyclopropyl, $R^4$ represents hydrogen; represents optionally cyano-, fluorine-, chlorine-, methoxy-, ethoxy-, n- or i-propoxy-, methylthio-, ethylthio-, n- or i-propylthio-, methylsulphinyl-, ethylsulphinyl-, methylsulphonyl-, or ethylsulphonyl-substituted methyl, ethyl, n- or i-propyl, or n-, i-, s-, or t-butyl; represents optionally fluorine-, chlorine-, and/or bromine-substituted propenyl, butenyl, propynyl, or butynyl; represents optionally fluorine-, chlorine-, or methyl-substituted cyclopropyl, cyclobutyl, cyclopentyl, cyclohexyl, cyclopropylmethyl, cyclobutylmethyl, cyclopentylmethyl, or cyclohexylmethyl; or represents optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenyl or phenylmethyl, and $R^5$ represents hydroxyl; represents optionally fluorine-, chlorine-, methoxy-, ethoxy-, n- or i-propoxy-substituted methoxy, ethoxy, n- or i-propoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, or n- or i-propylsulphonyloxy; represents optionally fluorine-, chlorine-, and/or bromine-substituted propenyloxy, butenyloxy, propynyloxy, or butynyloxy; or represents optionally nitro-, cyano-, fluorine-, chlorine-, bromine-, methyl-, ethyl-, n- or i-propyl-, trifluoromethyl-, methoxy-, ethoxy-, n- or i-propoxy-, difluoromethoxy-, trifluoromethoxy-, methylthio-, ethylthio-, n- or i-propylthio-, difluoromethylthio-, trifluoromethylthio-, methylsulphinyl-, ethylsulphinyl-, trifluoromethylsulphinyl-, methylsulphonyl-, ethylsulphonyl-, or trifluoromethylsulphonyl-substituted phenylmethoxy, phenylcarbonyloxy, phenylcarbonylmethoxy, or phenylsulphonyloxy.

5. A composition comprising one or more compounds of formula (I) according to claim 1 and one or more extenders and/or surfactants.

6. A method for controlling unwanted plants comprising allowing one or more compounds of formula (I) according to claim 1 to act on unwanted plants and/or their habitat.

7. A method for controlling unwanted plants comprising allowing a composition according to claim 5 to act on unwanted plants and/or their habitat.

* * * * *